United States Patent
Ueno et al.

(10) Patent No.: US 8,613,700 B2
(45) Date of Patent: Dec. 24, 2013

(54) BENDING MECHANISM

(75) Inventors: Haruhiko Ueno, Akiruno (JP); Yutaka Masaki, Mitaka (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/275,852

(22) Filed: Oct. 18, 2011

(65) Prior Publication Data

US 2012/0078054 A1 Mar. 29, 2012

Related U.S. Application Data

(63) Continuation of application No. PCT/JP2011/058100, filed on Mar. 30, 2011.

(30) Foreign Application Priority Data

Jul. 29, 2010 (JP) ................................. 2010-170988

(51) Int. Cl.
A61B 1/00 (2006.01)

(52) U.S. Cl.
USPC .......................................... 600/146; 600/149

(58) Field of Classification Search
USPC ......... 600/146, 147, 149, 137, 139, 141, 142, 600/144, 145, 150
See application file for complete search history.

(56) References Cited

U.S. PATENT DOCUMENTS

| | | | |
|---|---|---|---|
| 4,374,525 A * | 2/1983 | Baba | 600/463 |
| 4,503,842 A * | 3/1985 | Takayama | 600/152 |
| 5,551,945 A * | 9/1996 | Yabe et al. | 600/122 |
| 5,960,145 A * | 9/1999 | Sanchez | 385/116 |
| 6,905,461 B2 * | 6/2005 | Hino | 600/146 |
| 2002/0143238 A1 | 10/2002 | Hino et al. | |
| 2003/0018237 A1 | 1/2003 | Okada | |

FOREIGN PATENT DOCUMENTS

| | | |
|---|---|---|
| JP | A-5-309066 | 11/1993 |
| JP | A-8-224241 | 9/1996 |
| JP | A-2002-291687 | 10/2002 |
| JP | A-2005-65931 | 3/2005 |

OTHER PUBLICATIONS

Apr. 10, 2012 Supplementary European Search Report issued in Application No. 11799600.9.
International Search Report mailed Jun. 28, 2011 issued in International Patent Application No. PCT/JP2011/058100 (with translation).
Mar. 14, 2013 International Preliminary Report on Patentability issued in International Application No. PCT/JP2011/058100 (translation).

* cited by examiner

Primary Examiner — Alireza Nia
(74) Attorney, Agent, or Firm — Oliff & Berridge, PLC

(57) ABSTRACT

A bending mechanism includes a vertical driving portion with a central axis that extends along an X-axis direction, a horizontal driving portion with a central axis that extends along the X-axis direction and is adjacent to the vertical driving portion in a Y-axis direction, a vertical rotary portion that is coupled to the vertical driving portion and is rotated, and a horizontal rotary portion adjacent to the vertical rotary portion in the Y-axis direction that is coupled to the horizontal driving portion and is rotated. The binding mechanism further includes a holding portion holding a vertical operation wire extending from the vertical rotary portion to a rear surface on the side where the horizontal rotary portion is disposed, and holding a horizontal operation wire extending from the horizontal rotary portion to the rear surface on the side of the vertical rotary portion and further intersecting with a vertical operation wire.

11 Claims, 20 Drawing Sheets

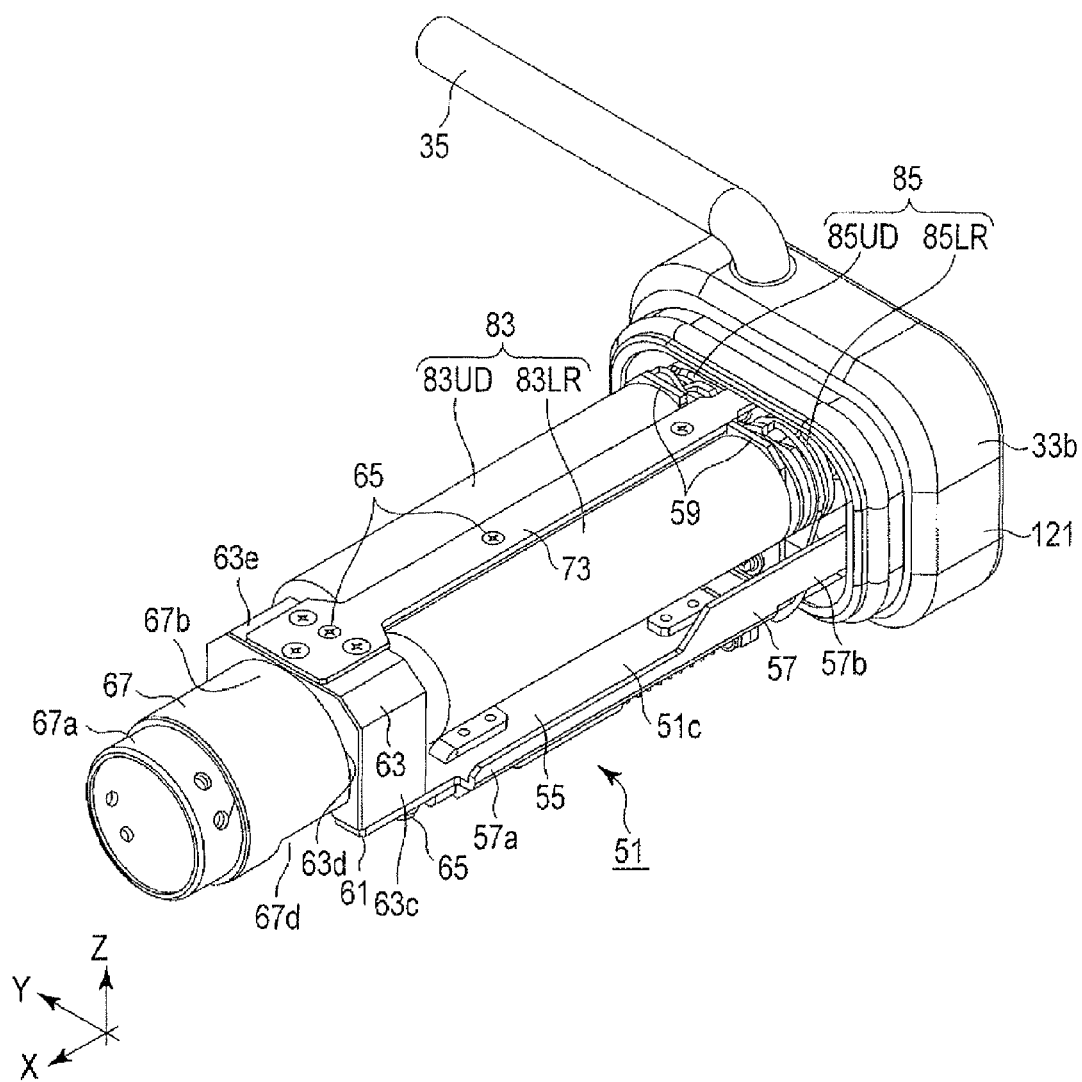
F I G. 3

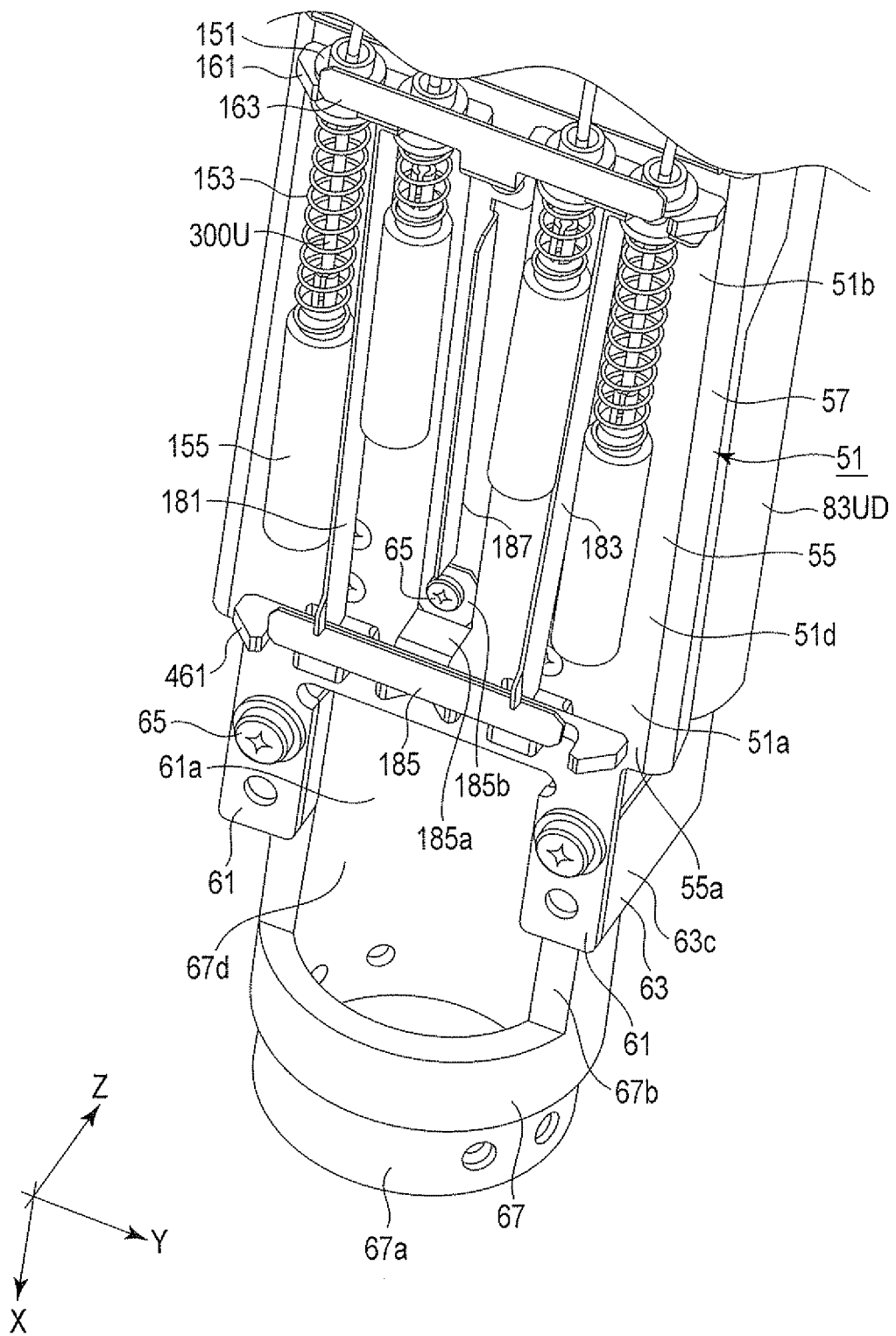
F I G. 4

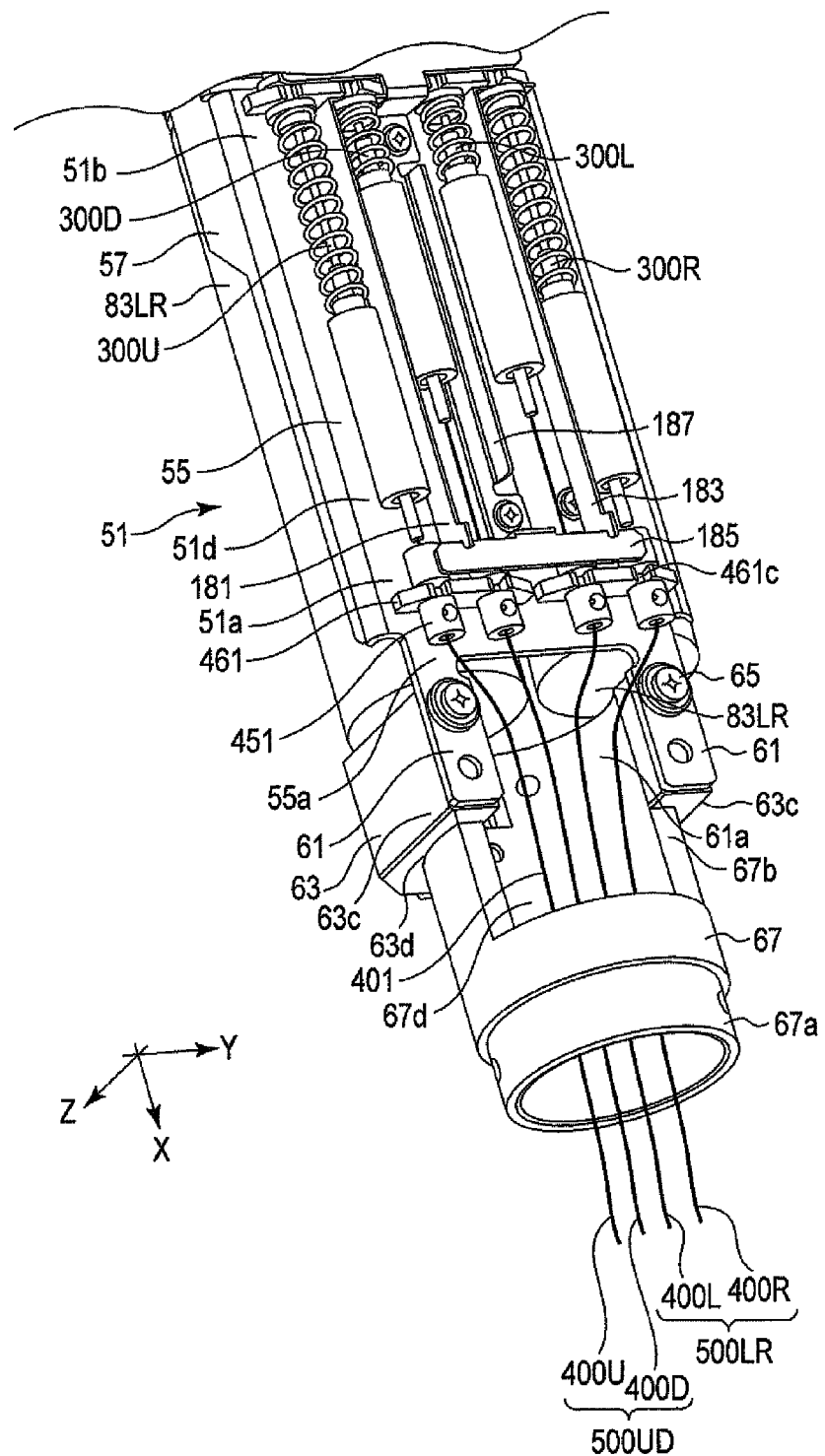
F I G. 5

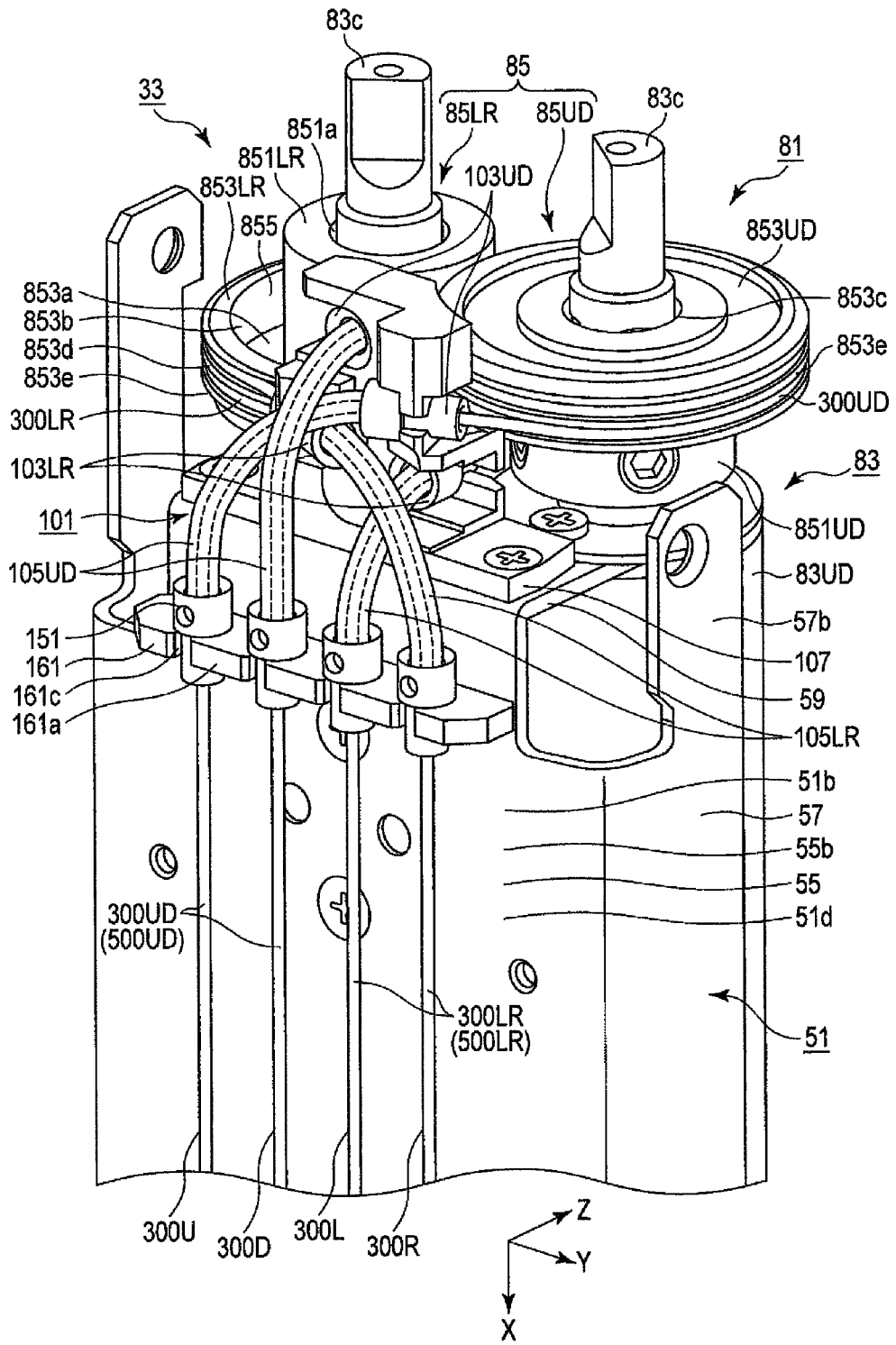
F I G. 6

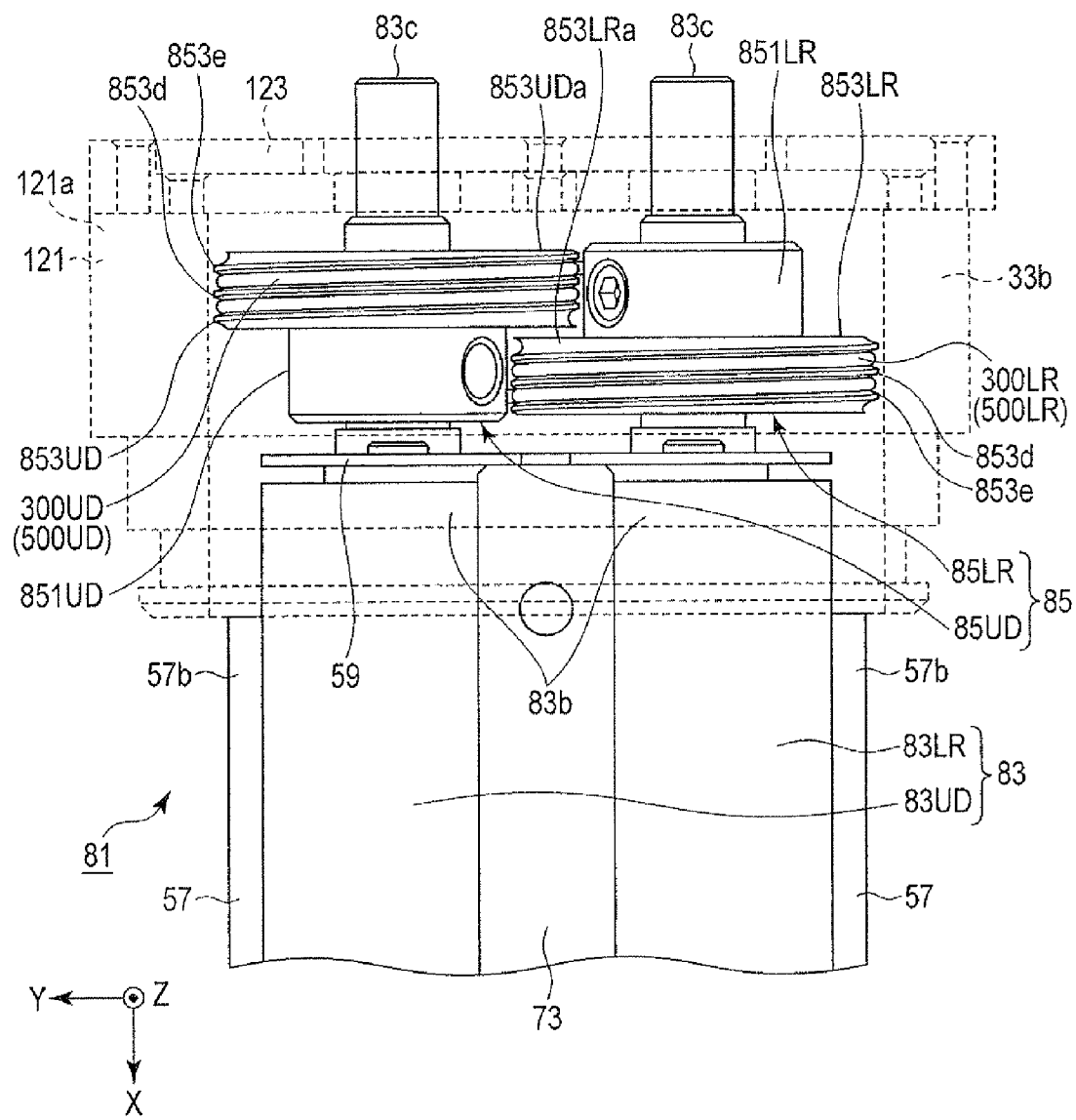
F I G. 7

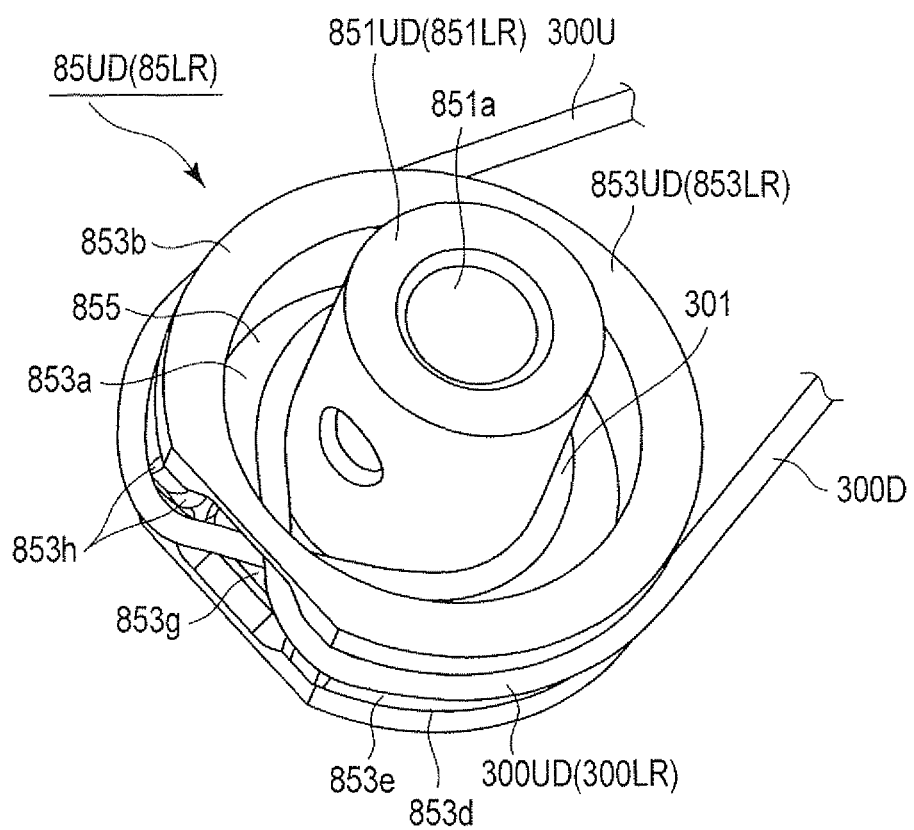
F I G. 10

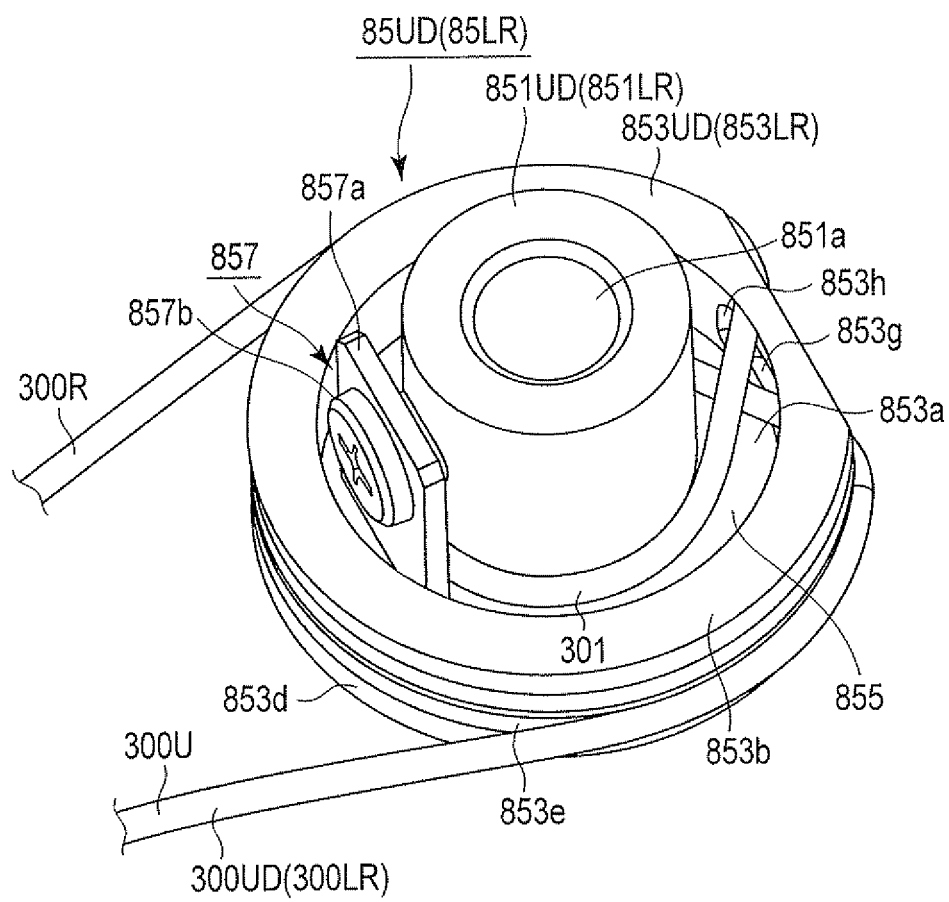
F I G. 11

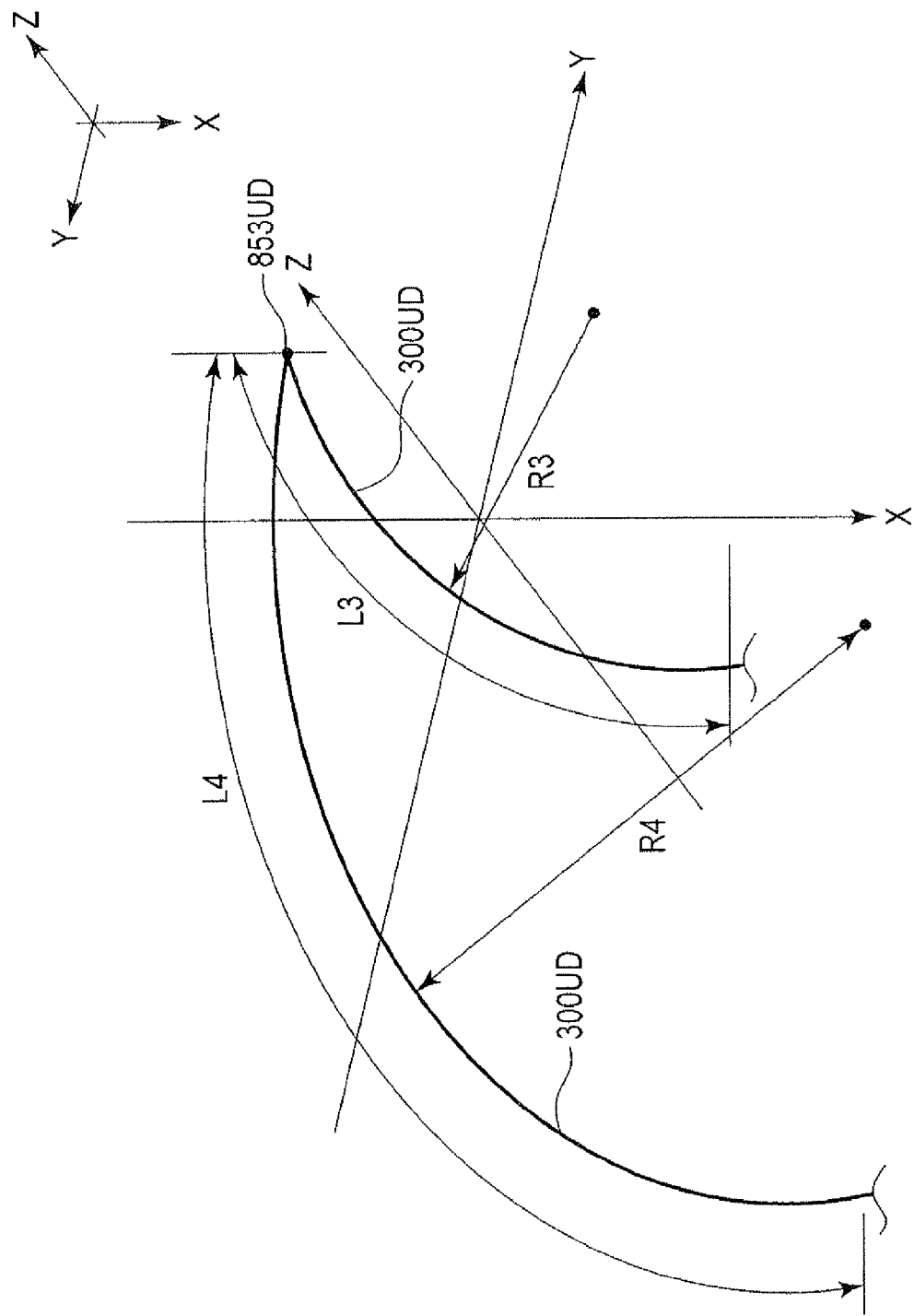
F I G. 13

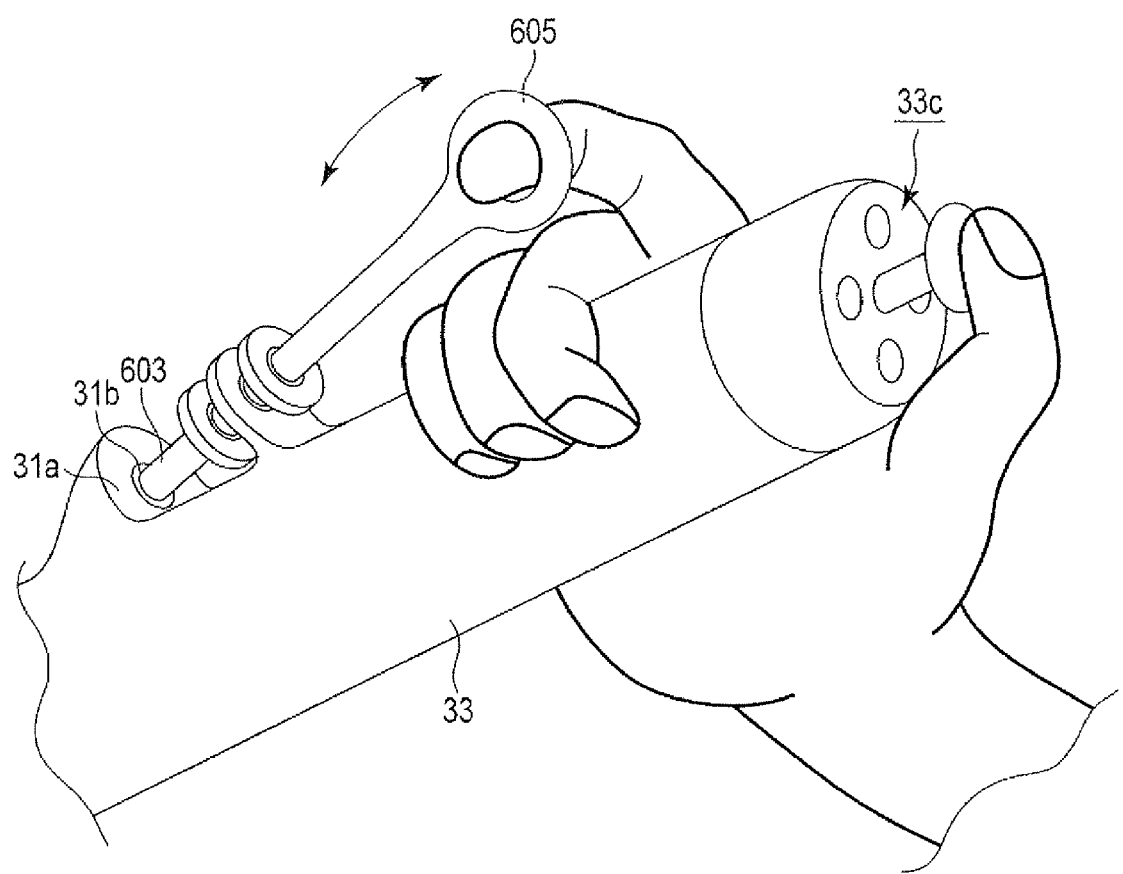
F I G. 21

BENDING MECHANISM

CROSS-REFERENCE TO RELATED APPLICATIONS

This application is a Continuation Application of PCT Application No. PCT/JP2011/058100, filed Mar. 30, 2011 and based upon and claiming the benefit of priority from prior Japanese Patent Application No. 2010-170988, filed Jul. 29, 2010, the entire contents of all of which are incorporated herein by reference.

BACKGROUND OF THE INVENTION

1. Field of the Invention

The present invention relates to a bending mechanism for bending a bending portion.

2. Description of the Related Art

In general, for example, an electric bending endoscope comprises an insertion portion to be inserted into a body cavity, and an operation portion for operating the endoscope. The insertion portion comprises a flexible tubular portion which has desired flexibility, a bending portion to be bent, and a distal hard portion. The operation portion comprises a bending mechanism for bending the bending portion.

Such an electric bending endoscope is disclosed in, for example, Jpn. Pat. Appln. KOKAI Publication No. 8-224241. Jpn. Pat. Appln. KOKAI Publication No. 8-224241 discloses a medical manipulator that allows the simplification of the structure of a driving portion and a reduction in size of the medical manipulator.

A bending mechanism of this medical manipulator comprises an operation wire connected to a bending portion, a pulley around which the operation wire is wound, and the driving portion such as a motor connected to the pulley. The driving portion uses its driving force to wind the pulley and pull the operation wire, thereby bending the bending portion.

BRIEF SUMMARY OF THE INVENTION

According to an aspect of embodiments, a bending mechanism which is disposed in a base plate and which vertically and horizontally bends a bending portion disposed in an insertion portion to be inserted into a body cavity, the bending mechanism comprising: a vertical driving portion which generates a vertical driving force to vertically bend the bending portion and which is disposed in a front surface of the base plate so that a central axis of the vertical driving, portion extends along the longitudinal direction of the insertion portion; a horizontal driving portion which generates a horizontal driving force to horizontally bend the bending portion and which is disposed in the front surface so that a central axis of the horizontal driving portion extends along the longitudinal direction and is adjacent to the vertical driving portion in a perpendicular direction perpendicular to the longitudinal direction; a vertical rotary portion which is coupled to the vertical driving portion and which is rotated by the vertical driving force and which is disposed on the side of the front surface; a horizontal rotary portion which is coupled to the horizontal driving portion and which is rotated by the horizontal driving force and which is disposed on the side of the front surface to be adjacent to the vertical rotary portion in the perpendicular direction; a vertical operation wire, the vertical operation wire being wound around the vertical rotary portion, extending toward a rear surface of the base plate from the vertical rotary portion, being disposed along the longitudinal direction in the rear surface, being connected to the bending portion, the vertical operation wire pulling the bending portion and vertically bending the bending portion when the vertical rotary portion is rotated by the vertical driving force; a horizontal operation wire, the horizontal operation wire being wound around the horizontal rotary portion, extending toward the rear surface from the horizontal rotary portion, being disposed along the longitudinal direction in the rear surface, being connected to the bending portion, the horizontal operation wire pulling the bending portion and horizontally bending the bending portion when the horizontal rotary portion is rotated by the horizontal driving force; and a holding portion which holds the vertical operation wire extending from the vertical rotary portion and the horizontal operation wire extending from the horizontal rotary portion so that the vertical operation wire extends from the vertical rotary portion to the rear surface on the side where the horizontal rotary portion is disposed and so that the horizontal operation wire extends from the horizontal rotary portion to the rear surface on the side of the vertical rotary portion and further intersects with the vertical operation wire when the vertical operation wire and the horizontal operation wire extend toward the rear surface.

According to an aspect of embodiments, a bending mechanism which is disposed in a base plate and which bends a bending portion disposed in an insertion portion to be inserted into a body cavity, the bending mechanism comprising: a driving portion which generates a driving force to bend the bending portion and which is disposed in a front surface of the base plate so that a central axis of the driving portion extends along the longitudinal direction of the insertion portion; a rotary portion which is coupled to the driving portion and which is rotated by the driving force and which is disposed on the side of the front surface; an operation wire, the operation wire being wound around the rotary portion, extending toward a rear surface of the base plate from the rotary portion, being disposed along the longitudinal direction in the rear surface, being connected to the bending portion, the operation wire pulling the bending portion and bending the bending portion when the rotary portion is rotated by the driving force; and a holding portion which holds the operation wire extending from the rotary portion so that one end of the operation wire and the other end thereof intersect with each other when the operation wire extends toward the rear surface.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a perspective view of a bending mechanism on the side of a driving portion when the bending mechanism is disposed on the base plate;

FIG. 4 is a perspective view of a grip portion on the side of operation wires when the bending mechanism is disposed on the base plate;

FIG. 5 is a perspective view of the grip portion on the side of the operation wires when the bending mechanism is disposed on the base plate;

FIG. 6 is a perspective view of the bending mechanism around a holding portion;

FIG. 7 is a front view of FIG. 6;

FIG. 10 is a perspective view of a rotary portion around which the operation wire is wound;

FIG. 11 is a perspective view when FIG. 10 is viewed from a different angle;

FIG. 13 is a view showing the relation between a length L3, a length L4, a bending radius R3, and a bending radius R4;

FIG. 21 is a perspective view showing how to grip the electric bending sheath to operate an endoscopic treatment tool.

DETAILED DESCRIPTION OF THE INVENTION

Figure 1:
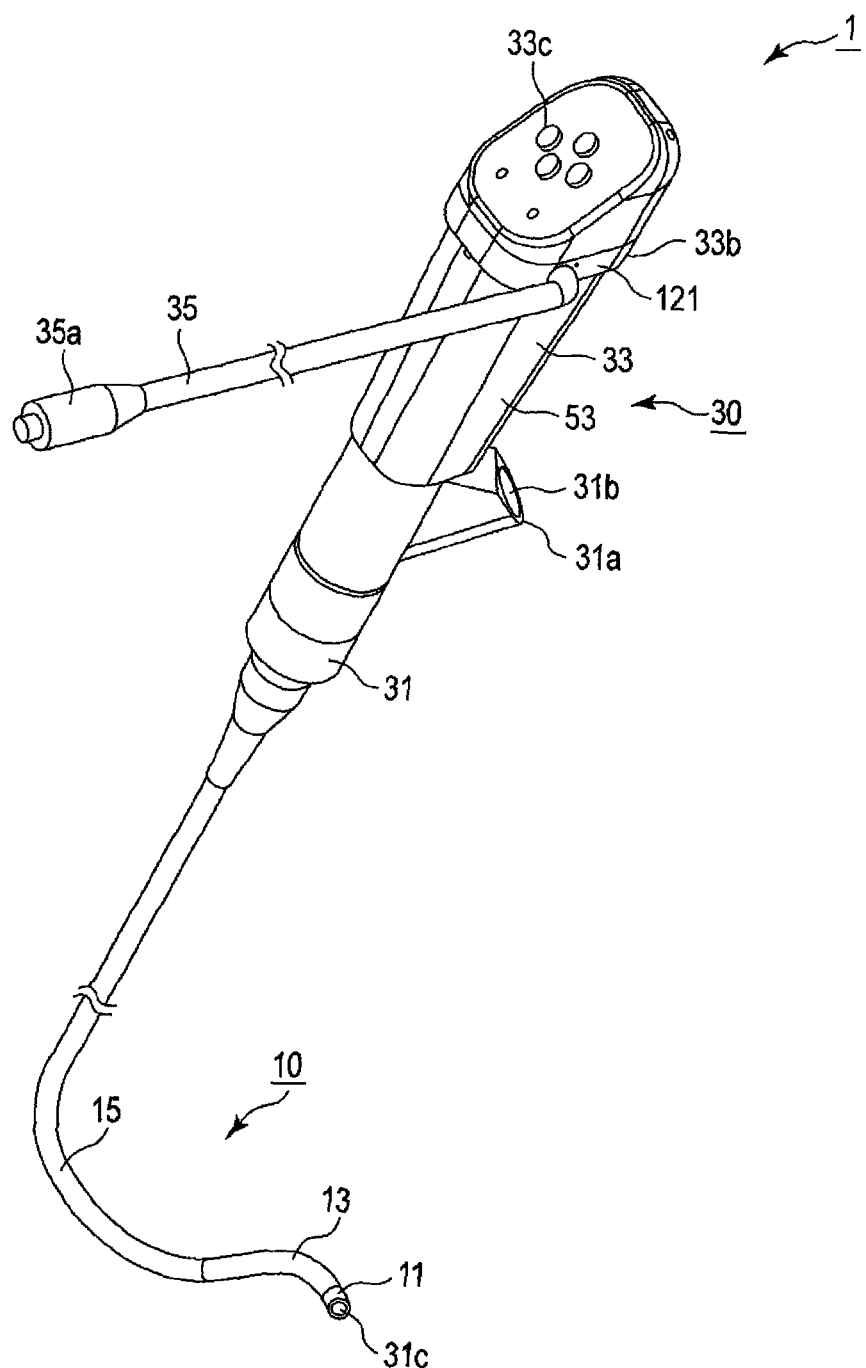
FIG. 1 is a perspective view of an electric bending endoscope according to an embodiment.

An embodiment of the present invention will be described in detail hereinafter with reference to the drawings.

The present embodiment is described with reference to FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, and FIG. 17. For the simplification of the drawings, some components are not shown in some of the drawings. For example, operation wires 400U, 400D, 400R, and 400L are not shown in FIG. 4.

Hereinafter, the longitudinal direction of an insertion portion 10, the longitudinal direction of a grip portion 33, the longitudinal direction of a base plate 51, the longitudinal direction of the operation wires 300UD, 300LR, 400U, 400D, 400R, and 400L, the axial direction of a driving portion 83, and the axial direction of a rotary portion 85 are in an X-axis direction. A direction perpendicular to the X-axis direction, the width direction of the grip portion 33, and the width direction of the base plate 51 are in a Y-axis direction. A direction perpendicular to the X-axis direction and the Y-axis direction is a Z-axis direction.

As shown in FIG. 1, an electric bending endoscope 1 (hereinafter referred to as an endoscope 1) according to the present embodiment comprises an insertion portion 10 to be inserted into a body cavity, and an operation portion 30 which is coupled to the proximal end of the insertion portion 10 and which operates the endoscope 1.

The insertion portion 10 comprises, from its distal end to its proximal end, a distal hard portion 11, a bending portion 13, and a flexible tubular portion 15. The proximal end of the distal hard portion 11 is coupled to the distal end of the bending portion 13. The proximal end of the bending portion 13 is coupled to the distal end of the flexible tubular portion 15.

The distal hard portion 11 is the distal end of the insertion portion 10, and is hard.

The bending portion 13 is bent in desired directions, for example, vertically and horizontally in accordance with the operation of a later-described bending operation portion 33c. The bending portion 13 is bent so that the position and direction of the distal hard portion 11 are changed, an observation target is taken into an observation view field, and illumination light is applied to the observation target. The bending portion 13 is connected to the later-described operation wires 400U, 400D, 400L, and 400R which extend through the flexible tubular portion 15.

The flexible tubular portion 15 has desired flexibility, and is bent by external force. The flexible tubular portion 15 is a tubular member that extends from a body 31 of the operation portion 30.

The operation portion 30 comprises the body 31 from which the flexible tubular portion 15 extends, the grip portion 33 which is coupled to the proximal end of the body 31 and which is gripped by an operator who operates the endoscope 1, and a universal cord 35 connected to the grip portion 33.

A treatment tool insertion hole 31a is provided in the body 31. The treatment tool insertion hole 31a is coupled to the proximal end of a treatment tool insertion channel 31b. In the insertion portion 10, the treatment tool insertion channel 31b is provided to extend from the flexible tubular portion 15 to the distal hard portion 11. The treatment tool insertion hole 31a is an insertion hole for inserting an unshown endoscopic treatment tool into the treatment tool insertion channel 31b. The unshown endoscopic treatment tool is inserted into the treatment tool insertion channel 31b from the treatment tool insertion hole 31a, and pushed into the side of the distal hard portion 11. The endoscopic treatment tool is then projected from a distal opening 31c of the treatment tool insertion channel 31b provided in the distal hard portion 11.

The universal cord 35 has a connection portion 35a connected to, for example, an unshown video processor or light source unit.

A proximal end 33b of the grip portion 33 is provided with the bending operation portion 33c for vertically and horizontally bending the bending portion 13. The bending operation portion 33c is a switch such as a TACT switch (registered trademark).

As shown in FIG. 1, the grip portion 33 is tapered toward the distal end. The grip portion 33 comprises the base plate 51 shown in FIG. 2, and a cover portion 53 shown in FIG. 1 covering the base plate 51. The body 31 is disposed at a distal end 51a of the base plate 51. The bending operation portion 33c is disposed at a proximal end 51b of the base plate 51.

Figure 2:
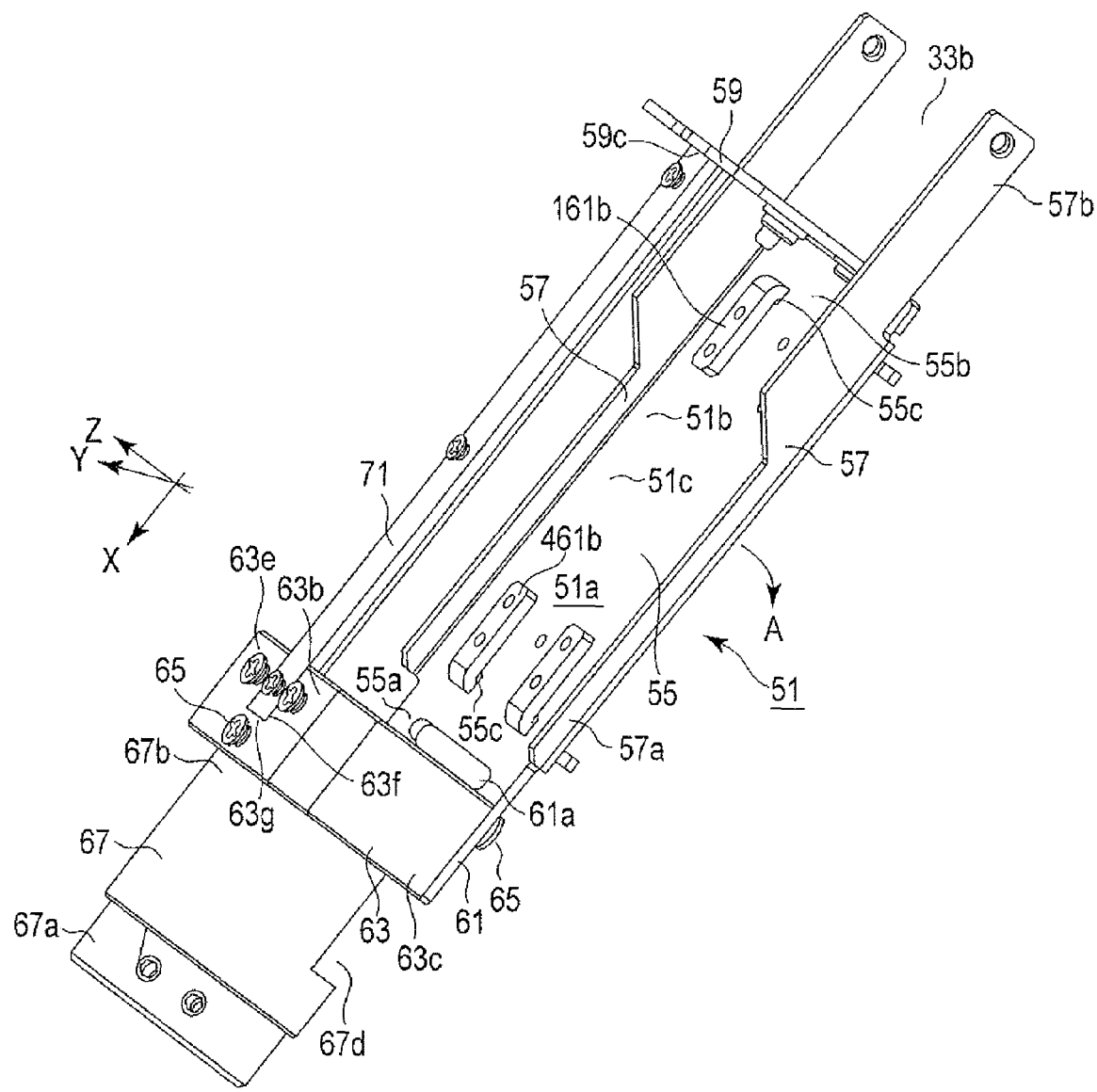
FIG. 2 is a perspective view of a base plate.

As shown in FIG. 2 and FIG. 3, the base plate 51 is, for example, a bottom board metal. As shown in FIG. 2, both sides of the base plate 51 are folded in the Z-axis direction from an XY plane, and the base plate 51 is recessed in section in the Y-axis direction. The proximal end 51b of the base plate 51 is also folded in the Z-axis direction in the same manner as the both sides. That is, the base plate 51 comprises a bottom plate 55, side plates 57 standing from the bottom plate 55 and integrated with the bottom plate 55, and an upper plate 59 standing from the bottom plate 55 and integrated with the bottom plate 55. As shown in FIG. 2, the surface of the bottom plate 55 where the side plates 57 and the upper plate 59 stand is a front surface 51c of the base plate 51. As shown in FIG. 4 and FIG. 5, the surface of the bottom plate 55 opposite to the front surface 51c is a rear surface 51d of the base plate 51.

As shown in FIG. 2, proximal ends 57b of the side plates 57 extend toward the proximal end 33b of the grip portion 33 than a proximal end 55b of the bottom plate 55, that is, from the upper plate 59, and project from the proximal end 55b of the bottom plate 55. The side plate 57 is thicker at its proximal end 57b than at its distal end 57a, and a step is formed between the proximal end 57b of the side plate 57 and the distal end 57a thereof.

As shown in FIG. 2 and FIG. 6, the upper plate 59 is provided in a space between the proximal ends 57b side of the side plates 57 in the Y-axis direction. The upper plate 59 has a contact surface 59c with which a later-described reinforcing member 71 comes into contact.

As shown in FIG. 2, FIG. 3, FIG. 4, and FIG. 5, the bottom plate 55 has, in a distal end 55a (distal end 51a) of the bottom plate 55, a pair of protrusions 61 that protrude from the distal end 55a toward the insertion portion 10. The protrusions 61 are integrated with the bottom plate 55. A part of the distal end 55a extends toward the insertion portion 10 so that the protrusions 61 are formed. The distal end 55a of the bottom plate 55 is recessed by the formation of the protrusions 61. An opening 61a which is open toward the insertion portion 10 is provided at the distal end 55a. The bottom plate 55 including the protrusions 61 is elastically deformable.

As shown in FIG. 2, FIG. 3, FIG. 4, and FIG. 5, a wall portion 63 is provided in the protrusions 61. The wall portion 63 is U-shaped so that a end 63c of the wall portion 63 contacts each of the pair of protrusions 61. As shown in FIG. 3 and FIG. 5, a groove 63d is formed in the wall portion 63. The end 63c of the wall portion 63 is fixed to each of the protrusions 61 by a fixing member 65, for example, a screw on the side of the rear surface 51d.

As shown in FIG. 2, FIG. 3, FIG. 4, and FIG. 5, a substantially cylindrical coupling member 67 which couples the grip portion 33 to the body 31 is fitted in the U-shaped wall portion 63, in other words, the groove 63d or the end 63c. A proximal end 67b of the coupling member 67 is fitted in the wall portion 63, and is fixed to the wall portion 63 by the fixing member 65, for example, a screw. A distal end 67a of the coupling member 67 is fitted in the body 31, and is fixed to the body 31 by a fixing member, for example, a screw. Thus, the coupling member 67 couples the grip portion 33 to the body 31.

As shown in FIG. 4 and FIG. 5, the substantially cylindrical coupling member 67 has a cut-out 67d cut toward the rear surface 51d. The cut-out 67d is provided to extend from the proximal end 67b of the coupling member 67 to the distal end 67a of the coupling member 67. When the coupling member 67 is fixed to the wall portion 63, the cut-out 67d is in communication with the opening 61a disposed between the protrusions 61. The width of the cut-out 67d is substantially equal to the width of the opening 61a, that is, the distance between the protrusions 61. The length of the cut-out 67d is greater than the length of the opening 61a, that is, the length of the protrusion 61.

As shown in FIG. 2, a recessed cut-out 63f is formed in an upper surface 63e of the wall portion 63. The cut-out 63f is open toward a proximal end 63b of the wall portion 63. The inner surface of the cut-out 63f is formed as a contact surface 63g with which the reinforcing member 71 comes into contact. The contact surface 63g is collinear with the contact surface 59c in the X-axis direction.

As shown in FIG. 2, the reinforcing member 71 in the shape of a single long plate is disposed between the contact surface 59c and the contact surface 63g. The reinforcing member 71 is disposed along the X-axis direction to contact the contact surface 59c and the contact surface 63g. The reinforcing member 71 reinforces the strength of the base plate 51, and warps the base plate 51.

Specifically, a length L1 of the reinforcing member 71 is slightly greater than a length L2 between the contact surface 59c and the contact surface 63g. When the reinforcing member 71 is disposed to contact the contact surface 59c and the contact surface 63g, the base plate 51 warps (curves) in the direction of an arrow A to change from L2 to L1 as shown in FIG. 2 such that the reinforcing member 71 is fitted into the space between the contact surface 59c and the contact surface 63g.

More specifically, L1 is slightly greater than L2. However, if the reinforcing member 71 is disposed between the contact surface 59c and the contact surface 63g, the base plate 51 warps in the direction of the arrow, so that the reinforcing member 71 is fitted into the space between the contact surface 59c and the contact surface 63g.

This warping is caused around the protrusions 61 where the opening 61a is formed and the strength is lower than in other parts. As the grip portion 33 is tapered, the base plate 51 is adapted to the shape of the grip portion 33 as a result of the warping.

As shown in FIG. 3, a support member 73 which supports the reinforcing member 71 and the wall portion 63 is disposed in the reinforcing member 71. The support member 73 is fixed to the reinforcing member 71 by the fixing member 65, for example, a screw, and further fixed to the wall portion 63 by the fixing member 65, for example, a screw.

As shown in FIG. 6, the grip portion 33 has a bending mechanism 81 which is disposed in the base plate 51 and which vertically and horizontally bends the bending portion 13. The bending mechanism 81 is covered with the cover portion 53 together with the base plate 51, and vertically and horizontally bends the bending portion 13 in conjunction with the operation of the bending operation portion 33c.

As shown in FIG. 3, FIG. 6, FIG. 7, FIG. 8, and FIG. 9, the bending mechanism 81 comprises the driving portion 83 which generates a driving force to bend the bending portion 13, and the rotary portion 85 which is coupled to the driving portion 83 and which is rotated by the driving force generated from the driving portion 83. As shown in FIG. 3, FIG. 6, FIG. 7, FIG. 8, and FIG. 9, the bending mechanism 81 also comprises operation wires 500UD and 500LR. The operation wires 500UD and 500LR are wound around the rotary portion 85, extend from the rotary portion 85 toward the rear surface 51d, are provided in the rear surface 51d along the X-axis direction, are connected to the bending portion 13, and pull the bending portion 13 and bend the bending portion 13 when the rotary portion 85 is rotated by the driving force.

As shown in FIG. 3, FIG. 6, and FIG. 7, the driving portion 83 is disposed in the front surface 51c. The driving portion 83 is surrounded by the upper plate 59, the side plates 57, the wall portion 63, and the reinforcing member 71 which prevent the driving portion 83 from dropping from the base plate 51.

As shown in FIG. 3 and FIG. 6, the driving portion 83 comprises a vertical driving portion 83UD and a horizontal driving portion 83LR.

The vertical driving portion 83UD generates a vertical driving force to vertically bend the bending portion 13. As shown in FIG. 3 and FIG. 6, the vertical driving portion 83UD is disposed in the front surface 51c of the base plate 51 so that a driving shaft 83c (central axis) of the vertical driving portion 83UD extends along the X-axis direction (the longitudinal direction of the insertion portion 10).

The horizontal driving portion 83LR generates a horizontal driving force to horizontally bend the bending portion 13. As shown in FIG. 3 and FIG. 6, the horizontal driving portion 83LR is disposed in the front surface 51*c* so that the driving shaft 83*c* (central axis) of the horizontal driving portion 83LR extends along the X-axis direction (the longitudinal direction of the insertion portion 10) and is adjacent to the vertical driving portion 83UD in the Y-axis direction.

The vertical driving portion 83UD and the horizontal driving portion 83LR are disposed symmetrically with respect to the central axis of the grip portion 33. The axial direction of the driving shaft 83*c* is the axial direction of the driving portion 83, the axial direction of the rotary portion 85, and the longitudinal direction of the insertion portion 10. These directions are in the same direction.

The vertical driving portion 83UD and the horizontal driving portion 83LR have the same structure and shape, and therefore, the vertical driving portion 83UD is described by way of example with reference to FIG. 3 and FIG. 6.

The vertical driving portion 83UD is cylindrical. The vertical driving portion 83UD is, for example, an actuator having a motor, a gear, and a position sensor.

As shown in FIG. 3, FIG. 6, and FIG. 7, the rotary portion 85 is disposed on the side of the front surface 51*c*. The rotary portion 85 is disposed closer to the proximal end 33*b* of the grip portion 33 than the upper plate 59, and protrudes from the upper plate 59.

The rotary portion 85 comprises a vertical rotary portion 85UD and a horizontal rotary portion 85LR.

The vertical rotary portion 85UD is coupled to the driving shaft 83*c* of the vertical driving portion 83UD, and is rotated by a vertical driving force generated from the vertical driving portion 83UD. The vertical rotary portion 85UD is disposed on the side of the front surface 51*c*.

The horizontal rotary portion 85LR is coupled to the driving shaft 83*c* of the horizontal driving portion 83LR, and is rotated by a horizontal driving force generated from the horizontal driving portion 83LR. The horizontal rotary portion 85LR is disposed on the side of the front surface 51*c* to be adjacent to the vertical rotary portion 85UD in the Y-axis direction.

As shown in FIG. 6, the operation wire 300UD, which is a vertical operation wire on the side of the grip portion 33 to vertically bend the bending portion 13, is wound around the vertical rotary portion 85UD. The operation wire 300UD is provided in the grip portion 33, and extends toward the rear surface 51*d* from the vertical rotary portion 85UD via the proximal end 55*b* of the bottom plate 55. Moreover, the operation wire 300UD is disposed in the rear surface 51*d* along the X-axis direction. As shown in FIG. 5, the operation wire 400U, which is an upward operation wire on the side of the insertion portion 10 to bend the bending portion 13 upward, is coupled to one end 300U of the operation wire 300UD on the side of the rear surface 51*d*. The operation wire 400D, which is a downward operation wire on the side of the insertion portion 10 to bend the bending portion 13 downward, is coupled to the other end 300D of the operation wire 300UD on the side of the rear surface 51*d*. The operation wire 400U and the operation wire 400D are inserted through the insertion portion 10, and are connected to the bending portion 13.

The operation wire 300UD, the operation wire 400U, and the operation wire 400D serve as the vertical operation wire 500UD to vertically bend the bending portion 13. Thus, the vertical operation wire 500UD is wound around the vertical rotary portion 85UD, extends toward the rear surface 51*d* of the base plate 51 from the vertical rotary portion 85UD, is disposed along the longitudinal direction in the rear surface 51*d*, and is connected to the bending portion 13. The vertical operation wire 500UD then pulls the bending portion 13 and vertically bends the bending portion 13 when the vertical rotary portion 85UD is rotated by the vertical driving force.

As shown in FIG. 6, the operation wire 300LR, which is a horizontal operation wire on the side of the grip portion 33 to horizontally bend the bending portion 13, is wound around the horizontal rotary portion 85LR. The operation wire 300LR is disposed in the grip portion 33, and extends toward the rear surface 51*d* from the horizontal rotary portion 85LR via the proximal end of the bottom plate 55. Moreover, the operation wire 300LR is disposed in the rear surface 51*d* along the X-axis direction. As shown in FIG. 5, the operation wire 400L, which is a leftward operation wire on the side of the insertion portion 10 to bend the bending portion 13 leftward, is coupled to one end 300L of the operation wire 300LR on the side of the rear surface 51*d*. The operation wire 400R, which is a rightward operation wire on the side of the insertion portion 10 to bend the bending portion 13 rightward, is coupled to the other end 300R of the operation wire 300LR on the side of the rear surface 51*d*. The operation wire 400L and the operation wire 400R are inserted through the insertion portion 10, and are connected to the bending portion 13.

The operation wire 300LR, the operation wire 400L, and the operation wire 400R serve as the horizontal operation wire 500LR to horizontally bend the bending portion 13. Thus, the horizontal operation wire 500LR is wound around the horizontal rotary portion 85LR, extends toward the rear surface 51*d* of the base plate 51 from the horizontal rotary portion 85LR, is disposed along the longitudinal direction in the rear surface 51*d*, and is connected to the bending portion 13. The horizontal operation wire 500LR then pulls the bending portion 13 and horizontally bends the bending portion 13 when the horizontal rotary portion 85LR is rotated by the horizontal driving force.

The vertical rotary portion 85UD and the horizontal rotary portion 85LR are described here.

As shown in FIG. 7, the vertical rotary portion 85UD is disposed closer to the proximal end 33*b* of the grip portion 33 than the vertical driving portion 83UD, and the horizontal rotary portion 85LR is disposed closer to the proximal end 33*b* of the grip portion 33 than the horizontal driving portion 83LR. The vertical rotary portion 85UD and the horizontal rotary portion 85LR are symmetrical with respect to the central axis of the grip portion 33. The central axis of the vertical rotary portion 85UD and the central axis of the horizontal rotary portion 85LR are disposed along the X-axis direction. The central axis of the vertical rotary portion 85UD is coaxial with the central axis (driving shaft 83*c*) of the vertical driving portion 83UD. The central axis of the horizontal rotary portion 85LR is coaxial with the central axis (driving shaft 83*c*) of the horizontal driving portion 83LR.

The vertical rotary portion 85UD and the horizontal rotary portion 85LR have the same structure and shape, and therefore, the structure of the vertical rotary portion 85UD is described by way of example with reference to FIG. 6, FIG. 7, FIG. 8, FIG. 9, and FIG. 10. In FIG. 10 and FIG. 11, a spiral groove 853*e* shown in FIG. 7 and the operation wire 300UD wound around the groove 853*e* more than once as shown in FIG. 7 are not shown for the simplification of the drawings.

The vertical rotary portion 85UD comprises a vertical bearing 851UD into which the driving shaft 83*c* of the vertical driving portion 83UD is fitted, and a vertical winding portion 853UD which is formed to be integrated with the vertical bearing 851UD and which is greater in diameter than the vertical bearing 851UD and the vertical driving portion 83UD and around which the vertical operation wire 500UD is wound.

In the drawings, the bearing in the horizontal rotary portion 85LR is a horizontal bearing 851LR, and the winding portion is shown as a horizontal winding portion 853LR. The horizontal operation wire 500LR is wound around the horizontal winding portion 853LR. The horizontal bearing 851LR has the same structure as the vertical bearing 851UD, and the horizontal winding portion 853LR has the same structure as the vertical winding portion 853UD.

Figure 12:
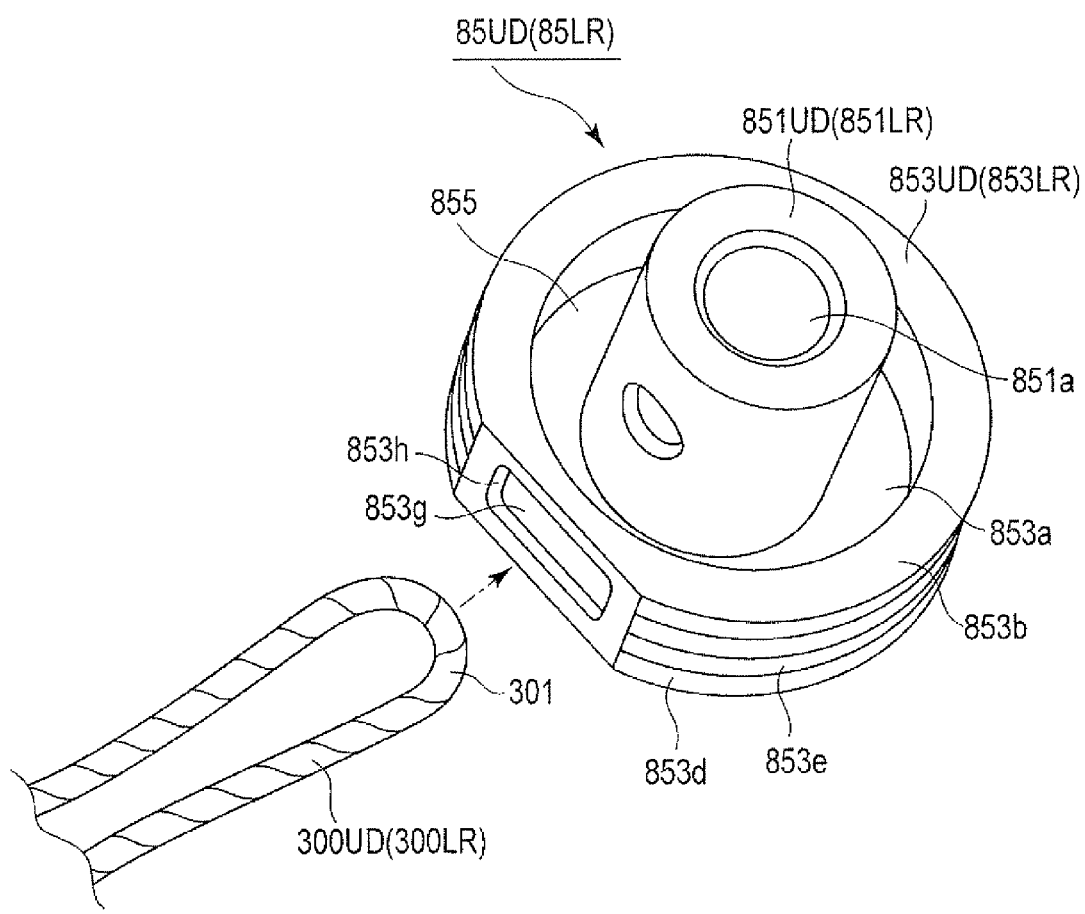
FIG. 12 is a view showing the operation wire to be wound around the rotary portion.

As shown in FIG. 10, FIG. 11, and FIG. 12, the vertical bearing 851UD is cylindrical, and has a bore 851a into which the driving shaft 83c of the vertical driving portion 83UD is fitted. The vertical bearing 851UD serves as a boss. The vertical bearing 851UD is higher than the vertical winding portion 853UD.

The vertical winding portion 853UD is substantially ring-shaped, and is greater in outside diameter than the vertical driving portion 83UD. A bottom surface 853a is provided in one end face of the vertical winding portion 853UD. The vertical bearing 851UD stands in the bottom surface 853a. As shown in FIG. 6, a bore 853c through which the driving shaft 83c passes and which is coaxial with the bore 851a is provided in the bottom surface 853a. The vertical winding portion 853UD is coaxial with the vertical bearing 851UD. As shown in FIG. 10, a peripheral wall 853b of the vertical winding portion 853UD surrounds the vertical bearing 851UD. Therefore, a space 855 is formed between the peripheral wall 853b and the vertical bearing 851UD. The operation wire 300UD is disposed in the space 855.

As shown in FIG. 6, the spiral groove 853e in which the operation wire 300UD is disposed is formed in an outer peripheral surface 853d of the peripheral wall 853b. In FIG. 10 and FIG. 11, the groove 853e is shown in a simplified form.

The spiral groove 853e is, for example, a thread groove. The groove 853e prevents the operation wire 300UD from being piled up on the outer peripheral surface 853d in the Z-axis direction and the X-axis direction. Such a vertical winding portion 853UD is, for example, a pulley.

As shown in FIG. 10 and FIG. 11, an opening 853g with which the space 855 is in communication and through which the operation wire 300UD can be inserted toward the space 855 is formed in the groove 853e. A curved surface 853h is formed in the opening 853g on the side of the groove 853e to reduce the abrasion of the operation wire 300UD caused by friction with the groove 853e.

As shown in FIG. 11, a fixing mechanism 857 is disposed in the space 855 to fix, to the vertical bearing 851UD, the operation wire 300UD which is inserted through the opening 853g and which is disposed in the space 855. The fixing mechanism 857 is, for example, a clamp. More specifically, the fixing mechanism 857 comprises a plate 857a disposed in the space 855, and a fixing member 857b, for example, a screw for fixing the plate 857a to the vertical bearing 851UD. When the operation wire 300UD is held between the plate 857a and the vertical bearing 851UD, the fixing member 857b fixes the plate 857a to the vertical bearing 851UD. As a result, the operation wire 300UD held between the plate 857a and the vertical bearing 851UD is fixed. The fixing mechanism 857 is disposed to be symmetrical to the opening 853g with respect to the vertical bearing 851UD. Thus, in the present embodiment, the operation wire 300UD is fixed not by, for example, solder but by the fixing mechanism 857, and is therefore easily replaced.

In the present embodiment, as shown in FIG. 7, one of the vertical winding portion 853UD and the horizontal winding portion 853LR is disposed closer to the driving portion 83 (the distal end side of the insertion portion 10) than the other so that a part 853UDa of the vertical winding portion 853UD and a part 853LRa of the horizontal winding portion 853LR overlap each other in the X-axis direction. Therefore, in the X-axis direction, for example, the vertical bearing 851UD is disposed closer to the vertical driving portion 83UD than the vertical winding portion 853UD, and the horizontal winding portion 853LR is disposed closer to the horizontal driving portion 83LR than the horizontal bearing 851LR. Thus, the width of the bending mechanism 81 in the Y-axis direction is reduced, so that the bending mechanism 81 is reduced in size.

In the meantime, the vertical winding portion 853UD is adjacent to the horizontal bearing 851LR in the Y-axis direction. Thus, for example, the horizontal bearing 851LR prevents the operation wire 300UD wound around the vertical winding portion 853UD from dropping from the groove 853e, and the horizontal bearing 851LR functions as a guide for the operation wire 300UD.

Similarly, the horizontal winding portion 853LR is adjacent to the vertical bearing 851UD in the Y-axis direction. Thus, for example, the vertical bearing 851UD prevents the operation wire 300LR wound around the horizontal winding portion 853LR from dropping from the groove 853e, and the vertical bearing 851UD functions as a guide for the operation wire 300LR.

Here, a method of winding the operation wire 300UD around the vertical rotary portion 85UD is described with reference to FIG. 10, FIG. 11, and FIG. 12.

As shown in FIG. 12, a loop 301 is formed in the linear operation wire 300UD. The loop 301 is inserted through the opening 853g toward the space 855 from the outside of the vertical winding portion 853UD, and hooked to the vertical bearing 851UD to surround the vertical bearing 851UD, as shown in FIG. 10 and FIG. 11. In this case, as shown in FIG. 10, one end 300U of the operation wire 300UD located on the right of the vertical bearing 851UD and the other end 300D of the operation wire 300UD located on the left of the vertical bearing 851UD are removed from the opening 853g. Moreover, as shown in FIG. 10, one end 300U is fitted into the groove 853e to contact the left curved surface 853h of the opening 853g. The other end 300D is fitted into the groove 853e to contact the right curved surface 853h of the opening 853g.

Thus, the operation wire 300UD is wound in an l-shape (γ-shape) in the vertical bearing 851UD and the vertical winding portion 853UD. That is, the operation wire 300UD inserted into the opening 853g is wound around the vertical bearing 851UD and then removed from the opening 853g in a direction that intersects with the insertion direction. That is, the operation wire 300UD inserted into the opening 853g and the operation wire 300UD removed from the opening 853g intersect with each other around the opening 853g.

The operation wire 300UD is not wound in an Ω-shape around the vertical bearing 851UD and the vertical winding portion 853UD. This prevents the operation wire 300UD from bending at an acute angle in the opening 853g, and prevents stress from concentrating on the edge of the opening 853g. As the curved surface 853h is formed, the abrasion of the operation wire 300UD is reduced.

In the case described above, in order to prevent the variation in the assembling precision of the operation wire 300UD, the loop 301 is formed so that a wire nozzle 151, an urging member 153, a coupling member 155, and a drop prevention member 157 that will be described later are disposed in the operation wire 300UD in advance, and the operation wire 300UD is wound.

Furthermore, the operation wire 300UD is fixed to the vertical bearing 851UD by the fixing mechanism 857. The operation wire 300UD is then extended to the rear surface 51*d* side from the vertical rotary portion 85UD via the proximal end 55*b* of the bottom plate 55.

A method of winding the operation wire 300LR around the horizontal rotary portion 85LR is similar to the above-described method of winding the operation wire 300UD. The operation wire 300LR is extended to the rear surface 51*d* side from the horizontal rotary portion 85LR via the proximal end 55*b* of the bottom plate 55 in the same manner as the operation wire 300UD.

Figure 8:
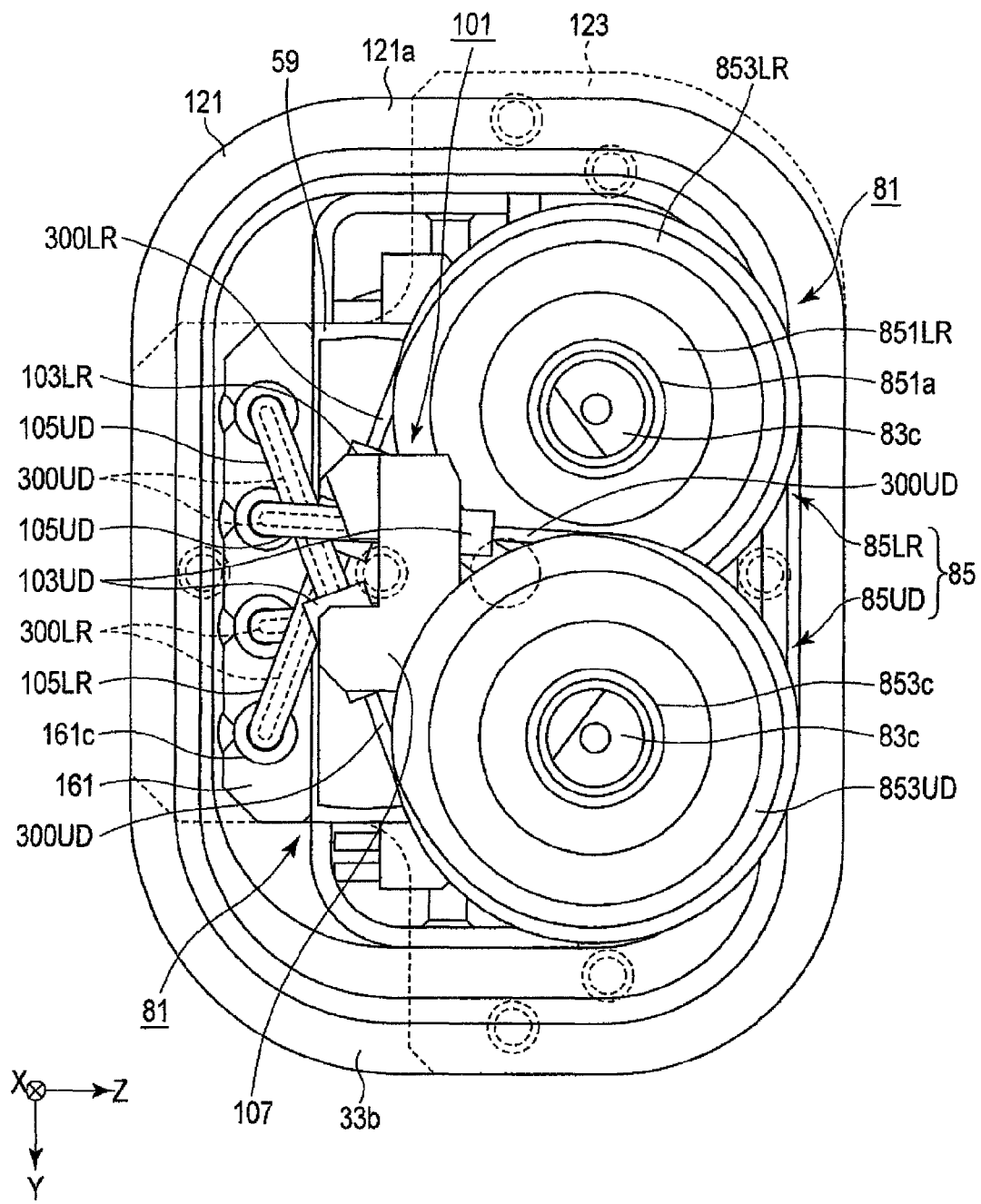
FIG. 8 is a top view of FIG. 6.

As shown in FIG. 6 and FIG. 8, the bending mechanism 81 comprises a holding portion 101 which holds the operation wire 300UD extending to the rear surface 51*d* from the vertical rotary portion 85UD and the operation wire 300LR extending to the rear surface 51*d* from the horizontal rotary portion 85LR. The holding portion 101 is disposed on the upper plate 59.

Specifically, the holding portion 101 holds the operation wire 300UD and the operation wire 300LR so that the operation wire 300UD extends from the vertical rotary portion 85UD to the rear surface 51*d* on the side where the horizontal rotary portion 85LR is disposed and so that the operation wire 300LR extends from the horizontal rotary portion 85LR to the rear surface 51*d* on the side of the vertical rotary portion 85UD and further intersects with the vertical operation wire 500UD.

In the present embodiment, the operation wire 300UD is not extended to the rear surface 51*d* from the vertical rotary portion 85UD along the Z-axis direction, and is not extended to the rear surface 51*d* where the vertical driving portion 83UD is disposed. In other words, the operation wire 300UD in the rear surface 51*d* is not adjacent to the vertical driving portion 83UD via the bottom plate 55 in the Z-axis direction.

In the present embodiment, as shown in FIG. 6 and FIG. 8, the holding portion 101 holds the operation wire 300UD so that the operation wire 300UD extends from the vertical winding portion 853UD in a direction tilted in the Z(Y)-axis direction and so that the operation wire 300UD extends to the rear surface 51*d* where the horizontal driving portion 83LR is disposed. That is, the holding portion 101 holds the operation wire 300UD so that the operation wire 300UD in the rear surface 51*d* is adjacent to the horizontal driving portion 83LR via the bottom plate 55 in the Z-axis direction.

Furthermore, in the present embodiment, the operation wire 300LR is not extended to the rear surface 51*d* from the horizontal winding portion 853LR along the Z-axis direction, and is not extended to the rear surface 51*d* where the horizontal driving portion 83LR is disposed. In other words, the operation wire 300LR in the rear surface 51*d* is not adjacent to the horizontal driving portion 83LR via the bottom plate 55 in the Z-axis direction.

In the present embodiment, as shown in FIG. 6 and FIG. 8, the holding portion 101 holds the operation wire 300UD so that the operation wire 300LR extends from the horizontal winding portion 853LR in a direction tilted in the Z(Y)-axis direction and so that the operation wire 300LR extends to the rear surface 51*d* where the vertical driving portion 83UD is disposed. That is, the holding portion 101 holds the operation wire 300LR so that the operation wire 300LR in the rear surface 51*d* is adjacent to the vertical driving portion 83UD via the bottom plate 55 in the Z-axis direction.

The holding portion 101 holds the operation wire 300UD and the operation wire 300LR so that the operation wire 300UD extending to the rear surface 51*d* from the vertical winding portion 853UD as described above intersects on the upper plate 59 with the operation wire 300LR extending to the rear surface 51*d* from the horizontal winding portion 853LR as described above. That is, the operation wire 300UD and the operation wire 300LR intersect with each other in the holding portion 101.

Moreover, the holding portion 101 holds the operation wire 300UD and the operation wire 300LR so that the extending direction of the operation wire 300UD extending from the vertical winding portion 853UD and the extending direction of the operation wire 400LD extending from the horizontal winding portion 853LR are tilted with respect to the Y-axis direction.

The longitudinal direction of the operation wire 300UD on the side of the rear surface 51*d* and the axial direction of the horizontal driving portion 83LR are symmetrical on the Z-axis to the longitudinal direction of the operation wire 300LR on the side of the rear surface 51*d* and the axial direction of the vertical driving portion 83UD.

Here, the relation between L3 and L4 is described with reference to FIG. 13. L3 indicates the length of the bent operation wire 300UD from the vertical winding portion 853UD to the rear surface 51*d* when the operation wire 300UD is extended to the rear surface 51*d* from the vertical winding portion 853UD along the Z-axis direction. L4 indicates the length of the bent operation wire 300UD from the vertical winding portion 853UD to the rear surface 51*d* when the operation wire 300UD is extended from the vertical winding portion 853UD in a direction tilted in the Z(Y)-axis direction as in the present embodiment.

In general, the length L4 is longer than the length L3, and a bending radius R4 in the length L4 is greater than a bending radius R3 in the length L3. As a result, in the bent operation wire 300UD, the burden on the operation wire 300UD when the operation wire 300UD is pulled in the case of the length L4 is less than the burden on the operation wire 300UD when the operation wire 300UD is pulled in the case of the length L3.

Therefore, the holding portion 101 holds the operation wire 300UD as described above. This holds true for the operation wire 300LR.

As shown in FIG. 6, the holding portion 101 comprises a vertical regulation portion 103UD, a vertical guide portion 105UD, a horizontal regulation portion 103LR, a horizontal guide portion 105LR, and a support member 107.

The vertical regulation portion 103UD regulates the extending direction of the operation wire 300UD so that the operation wire 300UD extends from the vertical winding portion 853UD in the tangential direction of the vertical winding portion 853UD tilted with respect to the Y-axis direction. The vertical regulation portion 103UD is, for example, a cylindrical wire nozzle through which the operation wire 300UD is inserted.

The operation wire 300UD regulated by the vertical regulation portion 103UD is inserted through the vertical guide portion 105UD. Thus, the vertical guide portion 105UD prevents interference between the operation wire 300UD and other components such as the operation wire 300LR. The vertical guide portion 105UD guides the operation wire 300UD so that the operation wire 300UD extends from the vertical winding portion 853UD to the rear surface 51*d* on the side of the horizontal rotary portion 85LR.

The vertical guide portion 105UD is bent toward the XY plane, for example, from a YZ plane. Thus, the vertical guide portion 105UD bends the operation wire 300UD so that the operation wire 300UD extended from the vertical winding portion 853UD and disposed in the YZ plane is disposed in the XY plane toward the rear surface 51*d*.

The vertical guide portion 105UD is, for example, a guide tube. The vertical guide portion 105UD is made of a bendable soft material. If the vertical guide portion 105UD is made of a hard material, the vertical guide portion 105UD is difficult to process and is thus costly. Moreover, the hard material causes trouble in the insertion of the operation wire 300UD, regulates the bending direction of the operation wire 300UD, and reduces the degree of freedom. However, if the vertical guide portion 105UD is made of a soft material, the operation wire 300UD can bend even after being inserted through the vertical guide portion 105UD. Thus, the vertical guide portion 105UD can increase the degree of freedom in the bending direction of the operation wire 300UD.

The vertical guide portion 105UD is disposed between the vertical regulation portion 103UD and the wire nozzle 151 which is held by a later-described holding member 161. The vertical guide portion 105UD may be movable in the axial direction of the operation wire 300UD or may be fixed to the vertical regulation portion 103UD.

The vertical regulation portion 103UD and the vertical guide portion 105UD are provided for one end 300U of the operation wire 300UD and the other end 300D of the operation wire 300UD, respectively.

The horizontal regulation portion 103LR regulates the extending direction of the operation wire 300LR so that the operation wire 300LR extends from the horizontal winding portion 853LR in the tangential direction of the horizontal winding portion 853LR tilted with respect to the Y-axis direction. The horizontal regulation portion 103LR is, for example, a cylindrical wire nozzle through which the operation wire 300LR is inserted.

The operation wire 300LR regulated by the horizontal regulation portion 103LR is inserted through the horizontal guide portion 105LR. Thus, the horizontal guide portion 105LR prevents interference between the operation wire 300LR and other components such as the operation wire 300UD. The horizontal guide portion 105LR guides the operation wire 300LR so that the operation wire 300LR extends from the horizontal winding portion 853LR to the rear surface 51d on the side of the vertical rotary portion 85UD and intersects with the operation wire 300UD.

The horizontal guide portion 105LR is bent toward the XY plane, for example, from the YZ plane. Thus, the horizontal guide portion 105LR bends the operation wire 300LR so that the operation wire 300LR extended from the horizontal winding portion 853LR and disposed in the YZ plane is disposed in the XY plane toward the rear surface 51d.

The horizontal guide portion 105LR is, for example, a guide tube. The horizontal guide portion 105LR is made of a bendable soft material in the same manner as the vertical guide portion 105UD.

The horizontal guide portion 105LR is disposed between the horizontal regulation portion 103LR and the wire nozzle 151 which is held by the later-described holding member 161. The horizontal guide portion 105LR may be movable in the axial direction of the operation wire 300LR or may be fixed to the horizontal regulation portion 103LR.

The horizontal regulation portion 103LR and the horizontal guide portion 105LR are provided for one end 300L of the operation wire 300LR and the other end 300R of the operation wire 300LR, respectively.

The support member 107 supports the vertical regulation portion 103UD and the horizontal regulation portion 103LR so that the vertical regulation portion 103UD and the horizontal regulation portion 103LR are located in the vicinity of the vertical winding portion 853UD and the horizontal winding portion 853LR. The support member 107 is fixed to the upper plate 59.

Figure 9:
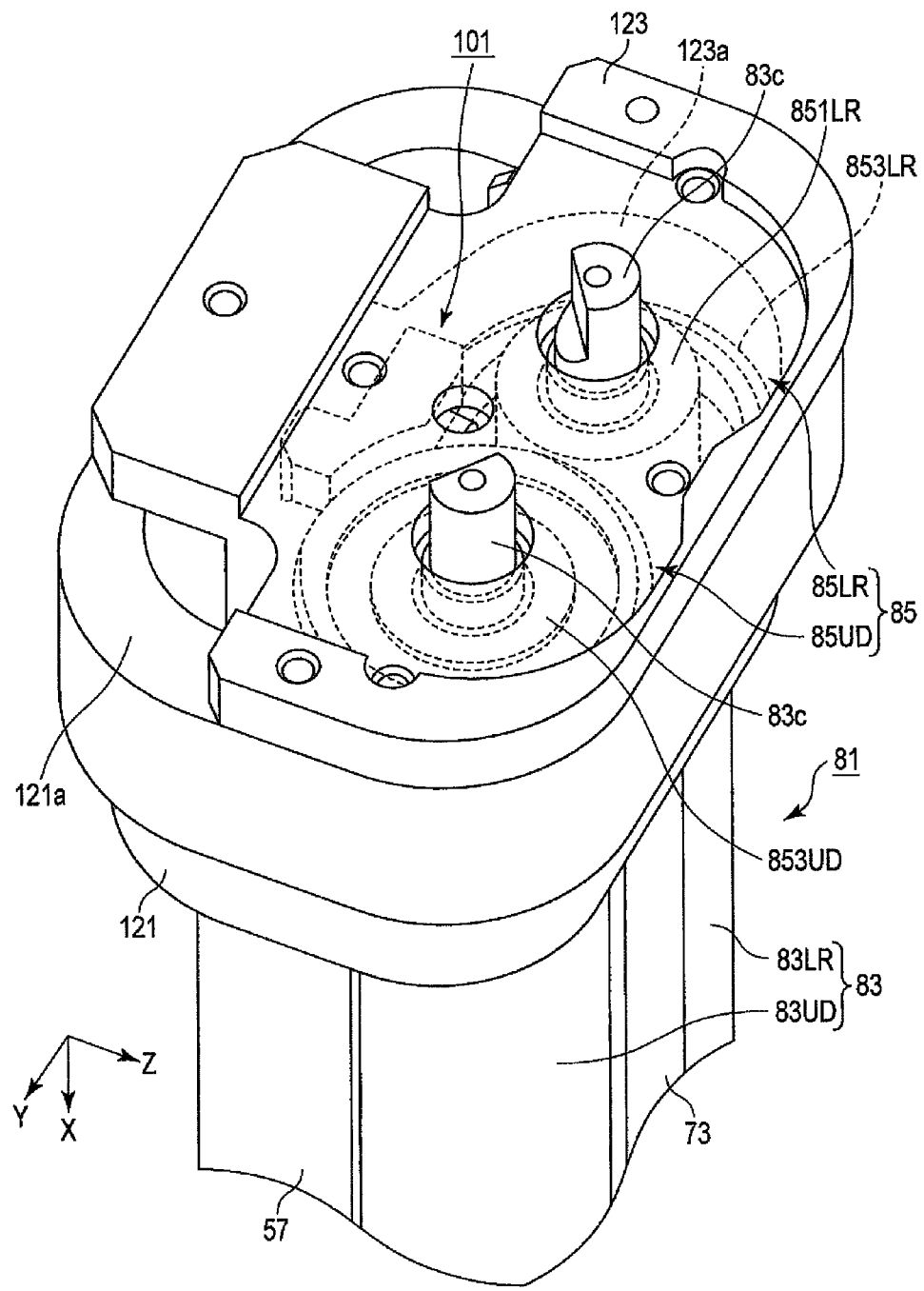
FIG. 9 is a perspective view of the bending mechanism from the front side.

As shown in FIG. 7, FIG. 8, and FIG. 9, the side of a proximal end 83b of the driving portion 83, the rotary portion 85, the holding portion 101, and the side of the proximal end 51b of the base plate 51 including the upper plate 59 are surrounded by a peripheral wall member 121 which is a first flange member.

A second flange member 123 is disposed on an upper surface 121a of the peripheral wall member 121. The second flange member 123 has a wall portion 123a which is fitted into the peripheral wall member 121 as shown in FIG. 9 when the second flange member 123 is disposed on the upper surface 121a. When fitted in, the wall portion 123a adjoins the groove 853e, and functions as a prevention wall for preventing the operation wire 300UD from dropping from the vertical winding portion 853UD and preventing the operation wire 300LR from dropping from the horizontal winding portion 853LR.

Now, the operation wire 300UD and the operation wire 300LR in the rear surface 51d are described with reference to FIG. 14, FIG. 15, and FIG. 16. As the operation wire 300UD and the operation wire 300LR have the same structure, the operation wire 300UD is described by way of example.

Figure 14:
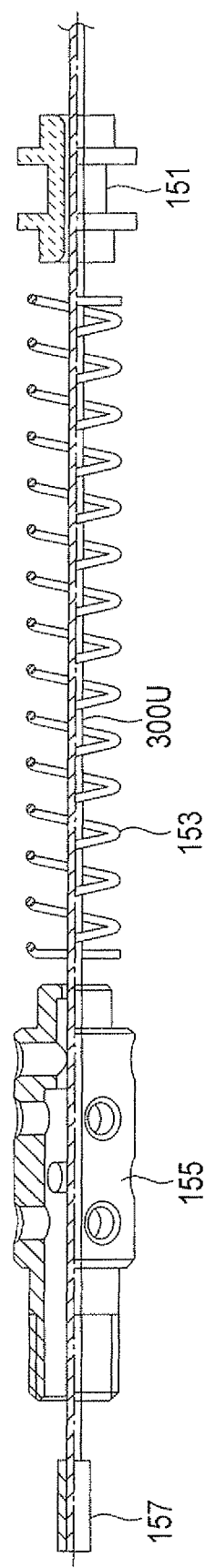
FIG. 14 is a view illustrating the configuration of one end of the operation wire.
Figure 15:
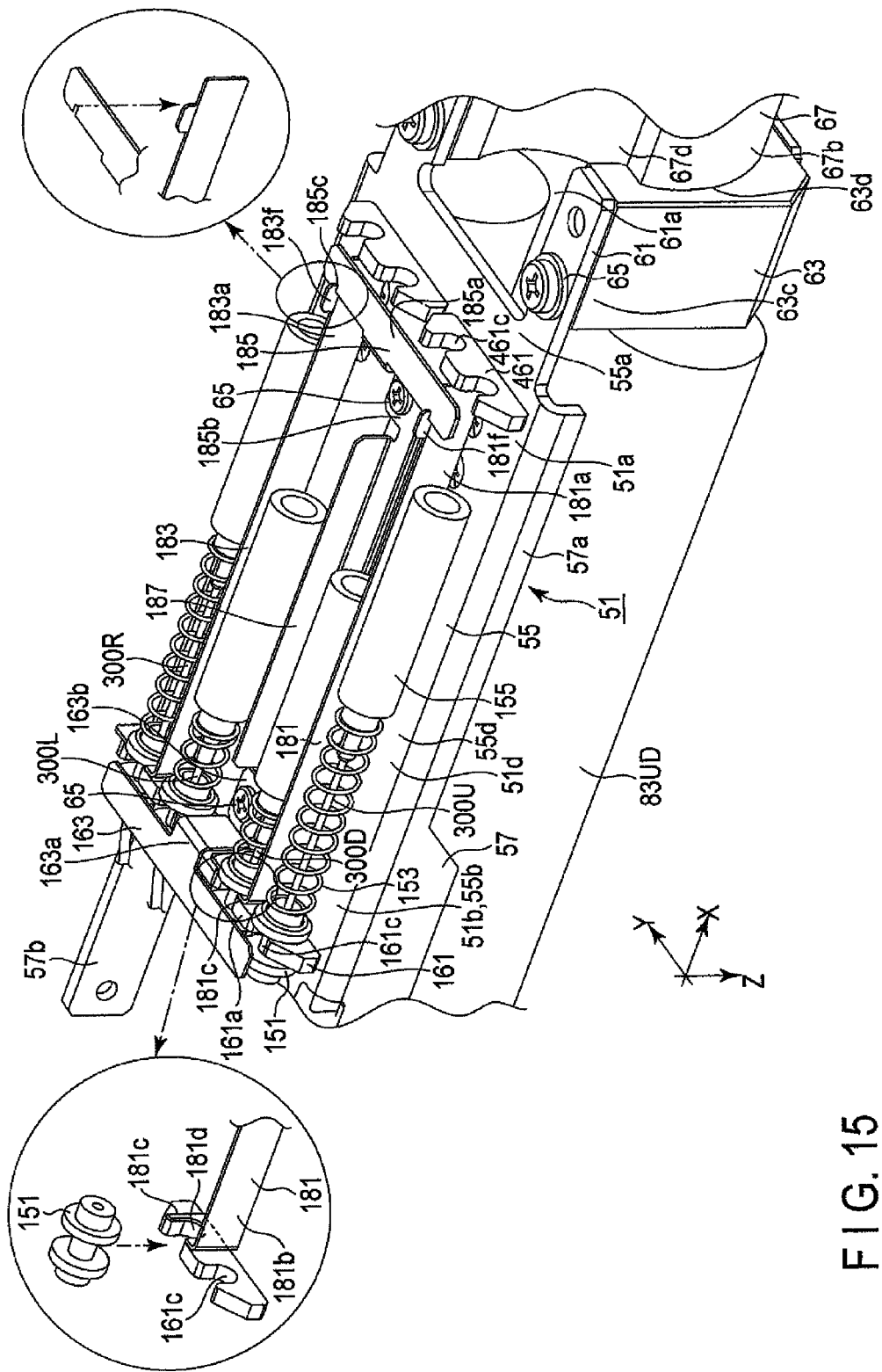
FIG. 15 is a perspective view illustrating the rear configuration of the base plate.
Figure 16:
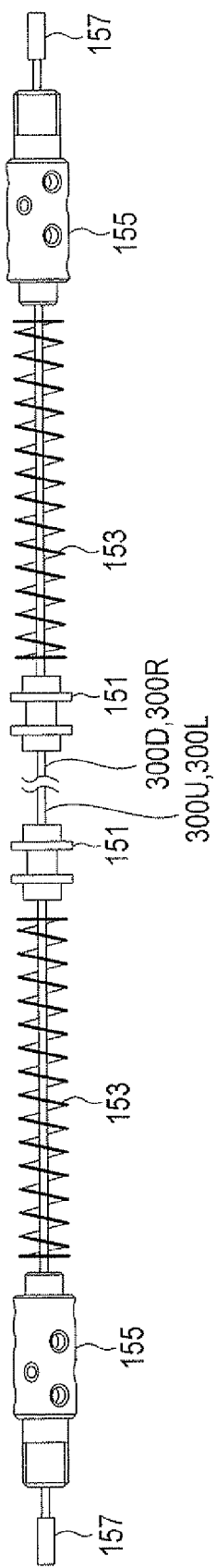
FIG. 16 is a view illustrating the configuration of both ends of the operation wire.

As shown in FIG. 14 and FIG. 15, the wire nozzle 151, the urging member 153, the coupling member 155, and the drop prevention member 157 are disposed at one end 300U of the operation wire 300UD from the side of the other end 300D to the side of one end 300U. The operation wire 300UD is inserted through the wire nozzle 151, the urging member 153, and the coupling member 155. The wire nozzle 151, the urging member 153, and the coupling member 155 are movable in the longitudinal direction of the operation wire 300UD, and the drop prevention member 157 is fixed to one end 300U. A wire nozzle 151, an urging member 153, a coupling member 155, and a drop prevention member 157 that are similar to those described above are also disposed on the other end 300D, as shown in FIG. 16.

As shown in FIG. 4, FIG. 5, FIG. 6, and FIG. 15, the wire nozzle 151 is held and positioned by the holding member 161. Thus, the wire nozzle 151 prevents the relaxation and meandering of the operation wire 300UD extended from the holding portion 101, and keeps the operation wire 300UD pulled toward the insertion portion 10. Moreover, the wire nozzle 151 regulates the traction direction of the operation wire 300UD in the rear surface 51d so that the traction direction of the operation wire 300UD in the rear surface 51d extends along the X-axis direction. The hardness of the wire nozzle 151 is higher than the hardness of the operation wire 300UD in order to prevent the abrasion of the operation wire 300UD caused by the wire nozzle 151.

The wire nozzle 151 through which the operation wire 300UD is inserted is positioned by the holding member 161 such that the operation wire 300UD ranging from the holding portion 101 to the wire nozzle 151 is pulled toward the insertion portion 10 side without relaxation and meandering.

As shown in FIG. 6 and FIG. 15, one end 161a of the holding member 161 has a recessed cut-out 161c into which the wire nozzle 151 is fitted. One end 161a of the holding member 161 is disposed at the proximal end 55b of the rear surface 55d to hold the wire nozzle 151. As shown in FIG. 2, in order to position the holding member 161, the other end 161b is inserted through the front surface 51c from the rear surface 51d via an opening 55c provided in the proximal end 55b, and folded in the front surface 51c.

The wire nozzle 151 is fitted into the cut-out 161c, and is thereby positioned in the X-axis direction and the Y-axis direction. As shown in FIG. 4 and FIG. 15, a prevention plate 163 is disposed in the rear surface 51d to prevent the wire nozzle 151 from dropping from the cut-out 161c in the Z-axis direction. The prevention plate 163 is disposed along the Y-axis direction to cover the cut-out 161c. As shown in FIG. 15, a part 163a substantially in the center of the prevention plate 163 in the Y-axis direction is folded in an L-shape toward the rear surface 51d, and is further folded in an L-shape to contact the rear surface 51d. The prevention plate 163 is fixed by the fixing member 65, for example, a screw in a folded portion 163b that contacts the rear surface 51d. The folded portion 163b extends along the X-axis direction, and is integrated with a partition plate 187 and a positioning plate 185 that will be described later.

The urging member 153 is, for example, a coil spring, and winds the operation wire 300UD. At least one urging member 153 is disposed at the end of the operation wire 300UD. The urging member 153 is held between the wire nozzle 151 and the coupling member 155. The urging member 153 urges the drop prevention member 157 against the wire nozzle 151 toward one end 300U via the coupling member 155, thereby urging, toward the insertion portion 10, the operation wire 300UD to which the drop prevention member 157 is fixed, and bringing the operation wire 300UD into close contact with the groove 853e. As a result, the vertical winding portion 853UD is prevented from turning idly, and the driving force of the vertical driving portion 83UD is transmitted to the operation wire 300UD without being wasted.

It is to be noted that the bending load of the operation wire 300UD<the minimum load of the urging member 153 and that the maximum load of the urging member 153≤the cutting strength of the operation wire 300UD/100.

It is also to be noted that the flexure length of the urging member 153 the traction length of the operation wire 300UD× 2.

The drop prevention member 157 prevents the wire nozzle 151, the urging member 153, and the coupling member 155 from dropping from the operation wire 300UD.

Figure 17:
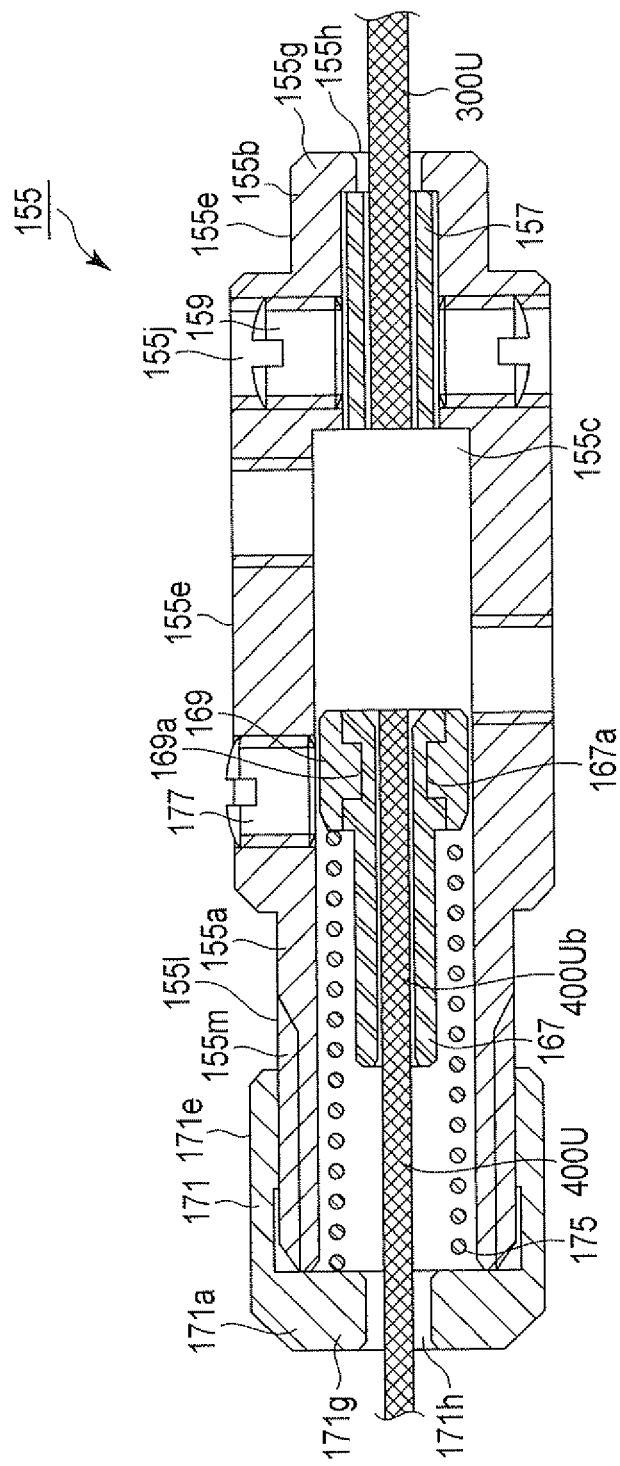
FIG. 17 is a sectional view of a coupling member.

The coupling member 155 couples, for example, one end 300U of the operation wire 300UD to the operation wire 400U. As shown in FIG. 17, the coupling member 155 is cylindrical. As shown in FIG. 17, the drop prevention member 157 fixed to one end 300U of the operation wire 300UD is disposed in an (internal) bore 155c of the coupling member 155.

A flat end face 155g formed substantially perpendicularly to the central axis direction of the coupling member 155 from a peripheral surface 155e is disposed at a proximal end 155b of the coupling member 155. An opening 155h through which the operation wire 300UD can be inserted is disposed in the end face 155g. The opening 155h is coaxial with the bore 155c, and the opening 155h is smaller in diameter than the bore 155c. The end face 155g serves as a prevention surface for preventing the drop prevention member 157 from coming out of the coupling member 155, and prevents the coupling member 155, the wire nozzle 151, and the urging member 153 from dropping from the operation wire 300UD. The end face 155g is urged by the above-mentioned urging member 153. This urging force urges the drop prevention member 157 in the end face 155g toward the insertion portion 10 via the end face 155g. Thus, the urging member 153 urges the operation wire 300UD toward the insertion portion 10 as described above.

Through-bores 155j which extend through the coupling member 155 to reach the inside (the bore 155c) are disposed in the peripheral surface 155e of the coupling member 155. The through-bores 155j are disposed at substantially equal intervals in the circumferential direction. The through-bores 155j are also disposed at equal intervals along the direction of the central axis of the coupling member 155. A positioning member 159 for positioning the drop prevention member 157 at the proximal end 155b is disposed in the through-bore 155j disposed closest to the proximal end 155b.

A thread groove 155m is formed in an outer peripheral surface 155l at a distal end 155a of the coupling member 155. A lock member 171, for example a nut is locked to the thread groove 155m. The lock member 171 has, at its distal end 171a, a flat end face 171g formed substantially perpendicularly to the central axis direction of the coupling member 155 from a peripheral surface 171e. An opening 171h through which the operation wire 400U can be inserted is disposed in the end face 171g. The opening 171h is coaxial with the bore 155c, and the opening 171h is smaller in diameter than the bore 155c. The end face 171g serves as a prevention surface for preventing a covering portion 167, a drop prevention member 169, and the operation wire 400U that will be described later from dropping out of the coupling member 155 (the bore 155c), and prevents the operation wire 400U from dropping from the coupling member 155.

A proximal end 400Ub of the operation wire 400U is covered with the covering portion 167. The covering portion 167 is slightly greater than the opening 171h. A recessed groove 167a is formed in the outer peripheral surface of the proximal end of the covering portion 167. The groove 167a is formed over the entire circumferential surface of the outer peripheral surface.

The C-shaped drop prevention member 169 is fitted in the covering portion 167. Specifically, a projecting portion 169a is formed in the entire inner peripheral surface of the drop prevention member 169, and the projecting portion 169a is fitted into the groove 167a. The outside diameter of the drop prevention member 169 is substantially the same as the diameter of the bore 155c.

The operation wire 400U including the covering portion 167 and the drop prevention member 169 is disposed in the bore 155c.

An urging member 175 for urging the operation wire 400U toward the proximal end 155b side of the coupling member 155 via the covering portion 167 and the drop prevention member 169 is disposed between the end face 171g of the lock member 171 and the drop prevention member 169. The urging member 175 urges the operation wire 400U toward the proximal end 155b side of the coupling member 155, and thereby prevents the loosening of the operation wire 400U and stretches the operation wire 400U. The urging member 175 winds the operation wire 400U and the covering portion 167, and is, for example, a coil spring. That is, the diameter of the urging member 175 is greater than the diameter of the operation wire 400U and the diameter of the covering portion 167, and is smaller than the diameter of the drop prevention member 169. The urging member 153 is replaceable.

When the urging member 175 urges the operation wire 400U, a positioning member 177 for positioning the operation wire 400U and others is disposed in the through-bore 155j. The positioning member 177 extends through the through-bore 155j and thus presses the drop prevention member 169, thereby positioning the operation wire 400U and others. Thus, the positioning of the operation wire 400U is adjusted in accordance with the position of the through-bore 155j, and there is no need for such work as soldering.

The coupling member 155 positions the drop prevention member 157 (the operation wire 300UD) by the positioning member 159, and positions the operation wire 400U by the positioning member 177, thereby indirectly coupling the operation wire 300UD to the operation wire 400U without, for example, soldering.

The allowable tension of the operation wires 300UD and 300LR is equal to or more than that of the operation wires 400U, 400D, 400L, and 400R.

The other end 300D of the operation wire 300UD, one end 300L of the operation wire 300LR, and the other end 300R of the operation wire 300LR are coupled to the operation wires 400D, 400L, and 400R in the same manner as described above.

As shown in FIG. 15, a partition plate 181 for preventing interference between the operation wires 300U and 300D is disposed between one end 300U of the operation wire 300UD and the other end 300D of the operation wire 300UD in the Y-axis direction. In the rear surface 51d, the partition plate 181 is a long slope disposed along the X-axis direction. A partition plate 183 similar in configuration to the partition plate 181 is also disposed between one end 300L of the operation wire 300LR and the other end 300R of the operation wire 300LR.

A proximal end 181b of the partition plate 181 is folded in an L-shape with respect to the X-axis direction to be substantially parallel to the Y-axis direction. A cut-out 181d into which the wire nozzle 151 is fitted is disposed in a folded portion 181c. The wire nozzle 151 is fitted into the cut-out 161c and the cut-out 181d so that the folded portion 181c is in contact with the holding member 161. As a result, the shaking of the proximal end 181b of the partition plate 181 in the X-axis direction, the Y-axis direction, and the Z-axis direction is prevented, and the proximal end 181b is positioned in the X-axis direction, the Y-axis direction, and the Z-axis direction. This holds true for the proximal end of the partition plate 183.

A distal end 181a of the partition plate 181 has a protrusion 181f protruding in the Z-axis direction. The positioning plate 185 having a cut-out 185c is mounted on the distal end 181a of the partition plate 181 and a distal end 183a of the partition plate 183. The protrusion 181f in the partition plate 181 and a protrusion 183f in the partition plate 183 are fitted into the cut-out 185c. The positioning plate 185 is mounted on the distal ends 181a and 183a along the Y-axis direction, and the cut-out 185c is fitted to the protrusions 181f and 183f. As a result, the shaking of the distal ends 181a and 183a in the X-axis direction, the Y-axis direction, and the Z-axis direction is prevented, and the distal ends 181a and 183a are positioned in the X-axis direction, the Y-axis direction, and the Z-axis direction.

In the same manner as the prevention plate 163, a part 185a substantially in the center of the positioning plate 185 in the Y-axis direction is folded in an L-shape toward the rear surface 51d, and is further folded in an L-shape to contact the rear surface 51d. The positioning plate 185 is fixed by the fixing member 65, for example, a screw in a folded portion 185b that contacts the rear surface 51d.

The partition plate 187 is disposed between the other end 300D side of the operation wire 300UD and one end 300L side of the operation wire 300LR in the Y-axis direction. The partition plate 187 is integrated with the prevention plate 163 (the folded portion 163b) and the positioning plate 185 (the folded portion 185b).

As shown in FIG. 5, a wire nozzle 451 similar to the wire nozzle 151 is provided in the operation wire 400U. In the same manner as the wire nozzle 151, this wire nozzle 451 is held and positioned by a holding member 461 similar to the holding member 161. One end of the holding member 461 has a recessed cut-out 461c into which the wire nozzle 451 is fitted. One end 461a of the holding member 461 is disposed at the distal end 55a on the side of the rear surface 51d to hold the wire nozzle 451. As shown in FIG. 2, in order to position the holding member 161, the other end 461b is inserted through the front surface 51c from the rear surface 51d via the opening 55c provided in the distal end 55a, and folded in the front surface 51c.

The wire nozzle 451 is fitted into the cut-out 461c, and is thereby prevented from shaking in the X-axis direction and the Y-axis direction and positioned in the X-axis direction and the Y-axis direction. The wire nozzle 451 is also prevented from dropping in the Z-axis direction by the positioning plate 185.

As shown in FIG. 5, the operation wire 400U is inserted through a coil pipe 401, and the coil pipe 401 prevents interference between the operation wire 400U and other components. The operation wire 400U and the coil pipe 401 are disposed in the coupling member 155 via the opening 61a and the cut-out 67d. The operation wire 400U and the coil pipe 401 are further disposed in the body 31 and in the insertion portion 10, and connected to the bending portion 13.

The operation wires 400D, 400L, and 400R are similar in configuration to the operation wire 400U.

Now, an operation method according to the present embodiment is described.

The operation wire 300UD is wound around the vertical rotary portion 85UD by the winding method described above, and extended from the vertical rotary portion 85UD. At the same time, the horizontal bearing 851LR and a wall portion 121b prevents the operation wire 300UD from dropping. The operation wire 300UD is wound more than once by the groove 853e.

The extending direction of the operation wire 300UD is regulated by the vertical regulation portion 103UD so that the operation wire 300UD extends in the tangential direction of the vertical rotary portion 85UD tilted in the Y-axis direction. Since the vertical regulation portion 103UD is supported by the support member 107, the movement of the extending direction of the operation wire 300UD is prevented.

The operation wire 300UD is further inserted through the vertical guide portion 105UD, and the vertical guide portion 105UD prevents interference between the operation wire 300UD and other components such as the operation wire 300LR. The operation wire 300UD is guided by the vertical guide portion 105UD so that the operation wire 300UD is bent toward the XY plane from the YZ plane and extended from the vertical rotary portion 85UD to the rear surface 51d where the horizontal rotary portion 85LR is disposed.

Thus, the length L4 is longer than the length L3, and the bending radius R4 in the length L4 is greater than the bending radius R3 in the length L3.

Thus, even if the axial direction of the vertical driving portion 83UD and the longitudinal direction of the insertion portion 10 are in the same direction, the operation wire 300UD is extended from the vertical rotary portion 85UD and then bent and connected to the bending portion 13 via the operation wires 400U and 400D, the load on the operation wire 300UD is reduced.

As the part 853UDa of the vertical winding portion 853UD and the part 853LRa of the horizontal winding portion 853LR overlap each other in the insertion direction, the bending mechanism 81 is reduced in size.

In the Y-axis direction, the vertical winding portion 853UD is adjacent to the horizontal bearing 851LR. Thus, the horizontal bearing 851LR prevents the operation wire 300UD from dropping from the groove 853e, and the operation wire 300UD is guided without dropping.

The operation wire 300UD is disposed in the spiral groove 853e, and is therefore wound therearound more than once. The rotary portion 85 is bigger than the driving portion 83. This ensures a bending amount. The groove 853e prevents the operation wire 300UD from being piled up on the outer peripheral surface 853d in the Z-axis direction and the X-axis direction.

While the operation wire 300UD has been described above, the same applies to the operation wire 300LR.

As described above, according to the present embodiment, the longitudinal direction of the insertion portion 10, the longitudinal direction of the vertical operation wire 500UD, the longitudinal direction of the horizontal operation wire 500LR, the axial direction of the driving portion 83, and the axial direction of the rotary portion 85 are in the same direction. Thus, the bending mechanism 81 can be smaller than when the axial direction of the driving portion 83 is perpendicular to the longitudinal direction of the insertion portion 10.

Furthermore, the operation wire 300UD and the operation wire 300LR are held by the holding portion 101 so that the operation wire 300UD extends from the vertical rotary portion 85UD to the rear surface 51d where the horizontal rotary portion 85LR is disposed and so that the operation wire 300LR extends from the horizontal rotary portion 85LR to the rear surface 51d on the side of the vertical rotary portion 85UD and further intersects with the operation wire 300UD when the operation wires 300UD and 300LR extending from the rotary portion 85 are bent toward the rear surface 51d.

Consequently, according to the present embodiment, the length L4 is longer than the length L3, and the bending radius R4 in the length L4 is greater than the bending radius R3 in the length L3, as shown in FIG. 13. Thus, according to the present embodiment, even if the operation wires 300UD and 300LR in the grip portion 33 are pulled to bend the bending portion 13, the load on the operation wires 300UD and 300LR is reduced, and the breakage of the operation wires 300UD and 300LR can be prevented.

According to the present embodiment, the part 853UDa of the vertical winding portion 853UD and the part 853LRa of the horizontal winding portion 853LR are disposed to overlap each other in the X-axis direction, so that the bending mechanism 81 can be reduced in size.

According to the present embodiment, in the Y-axis direction, the vertical winding portion 853UD is adjacent to the horizontal bearing 851LR, and the horizontal winding portion 853LR is adjacent to the vertical bearing 851UD. Thus, the dropping of the operation wires 300UD and 300LR from the groove 853e can be prevented, and the operation wires 300UD and 300LR can be guided without dropping.

According to the present embodiment, the spiral groove 853e is formed. Thus, the operation wires 300UD and 300LR can be wound around the winding portions 853UD and 853LR more than once, and the traction amount of the operation wires 300UD and 300LR can be ensured, and the bending amount of the bending portion 13 can be ensured.

According to the present embodiment, the groove 853e prevents the operation wires 300UD and 300LR from being piled up in the X-axis direction. Thus, according to the present embodiment, the rotary portion 85 is prevented from turning idly.

According to the present embodiment, the base plate 51 can be warped by the reinforcing member 71, the base plate 51 can be adapted to the shape of the grip portion 33.

According to the present embodiment, the driving portion 83 is surrounded by the side plates 57, the upper plate 59, the wall portion 63, and the reinforcing member 71. This makes it possible to prevent the driving portion 83 from dropping from the base plate 51.

According to the present embodiment, the operation wires 300UD and 300LR are wound in an l-shape (γ-shape) in the bearings 851UD and 851LR and the winding portions 853UD and 853LR. This makes it possible to prevent the operation wires 300UD and 300LR from bending at an acute angle, prevent stress from concentrating on the edge of the opening 853g, and prevent the breakage of the operation wires 300UD and 300LR. Moreover, according to the present embodiment, the curved surface 853h is formed in the opening 853g so that the abrasion of the operation wires 300UD and 300LR can be reduced.

According to the present embodiment, the operation wires 300UD and 300LR are fixed to the bearings 851UD and 851LR not by, for example, solder but by the fixing mechanism 857, and the operation wires 300UD and 300LR can therefore be easily replaced.

According to the present embodiment, when the operation wires 300UD and 300LR are wound around the rotary portions 85UD and 85LR, the variation in the assembling precision of the operation wires 300UD and 300LR can be prevented by disposing the wire nozzle 151, the urging member 153, the coupling member 155, and the drop prevention member 157 in the operation wires 300UD and 300LR in advance.

According to the present embodiment, the relaxation and meandering of the operation wires 300UD and 300LR extended from the rotary portions 85UD and 85LR to the wire nozzle 151 can be prevented by the wire nozzle 151 and the holding member 161, and the operation wires 300UD and 300LR can be pulled toward the insertion portion 10. Further, according to the present embodiment, the traction direction of the operation wires 300UD and 300LR can be regulated by the wire nozzle 151. Still further, according to the present embodiment, the wire nozzle 151 is harder than the operation wires 300UD and 300LR, so that the abrasion of the operation wires 300UD and 300LR caused by the wire nozzle 151 can be prevented.

According to the present embodiment, the operation wires 300UD and 300LR are urged toward the insertion portion 10 by the urging member 153. This makes it possible to bring the operation wires 300UD and 300LR into close contact with the groove 853e, and prevent the winding portions 853UD and 853LR from turning idly. Thus, the driving force of the driving portion 83 can be transmitted to the operation wires 300UD and 300LR without being wasted.

According to the present embodiment, the operation wires 300UD and 300LR can be easily and quickly coupled to the operation wires 400U, 400D, 400L, and 400R by the coupling member 155 without, for example, soldering.

According to the present embodiment, as the urging member 175 is replaceable, the operation wires 400U, 400D, 400L, and 400R can be kept stretched with high quality.

According to the present embodiment, the allowable tension of the operation wires 300UD and 300LR is equal to or more than that of the operation wires 400U, 400D, 400L, and 400R. This makes it possible to ease the concentration of stress caused when the operation wires 300UD and 300LR are bent at the proximal ends, and prevent the breakage of the operation wires 300UD and 300LR.

According to the present embodiment, interference between the operation wires 300U, 300D, 300L, and 300R can be prevented by the partition plates 181, 183, and 187. Further, according to the present embodiment, the partition plates 181 and 183 can be positioned in the X-axis direction, the Y-axis direction, and the Z-axis direction by the holding member 161, the wire nozzle 151, the prevention plate 163, the protrusion 181f, and the positioning plate 185.

According to the present embodiment, the wall portion 121b can prevent the operation wires 300UD and 300LR from dropping from the winding portions 853UD and 853LR.

According to the present embodiment, when the bending portion 13 only bends, for example, in the vertical direction, the bending mechanism 81 comprises the vertical driving portion 83UD, the vertical rotary portion 85UD, and the vertical operation wire 500UD. In this case, the holding portion 101 has only to hold the operation wire 300UD extended from the vertical rotary portion 85UD so that one end 300U of the operation wire 300UD and the other end 300D thereof intersect with each other when the vertical operation wire 500UD (300UD) extends toward the rear surface 51d. Moreover, in this case, the holding portion 101 holds the operation wire 300UD so that the operation wire 300UD is extended from the vertical winding portion 853UD in a direction tilted in the Z(Y)-axis direction and so that the operation wire 300UD is extended to the rear surface 51d disposed on the side to be tilted in the Z(Y)-axis direction.

Figure 18:
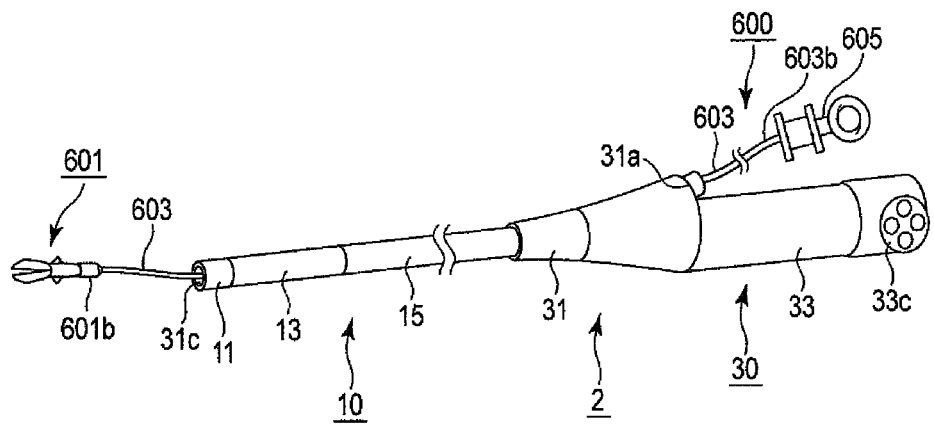
FIG. 18 is a perspective view of an electric bending sheath.

The bending mechanism 81 according to the present embodiment may also be used in an electric bending sheath 2 shown in FIG. 18 that is substantially similar in configuration to the above-mentioned endoscope 1. In this case, an endoscopic treatment tool 600 comprises a treatment portion 601 which treats an affected part and which is fitted into the distal opening 31c, a wire 603 which is coupled to a proximal end 601b of the treatment portion 601 and which is inserted from the distal opening 31c and removed from the treatment tool insertion hole 31a through the treatment tool insertion channel 31b, and an operation portion 605 which operates the treatment portion 601 and which is removably connected to a proximal end 603b of the wire 603 removed from the treatment tool insertion hole 31a.

Figure 19:
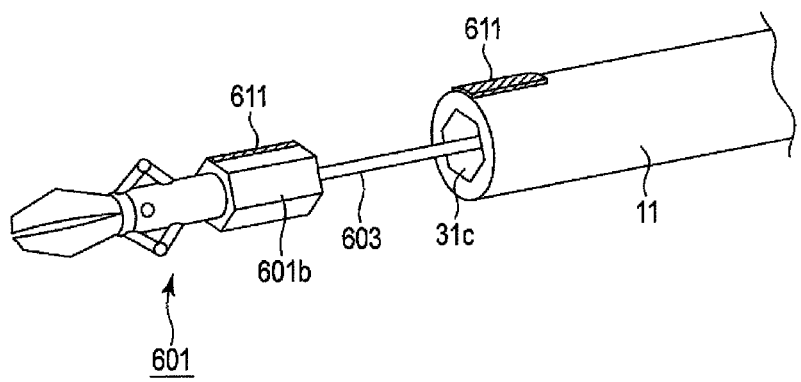
FIG. 19 is a view showing indexes in a treatment portion and a distal hard portion.
Figure 20:
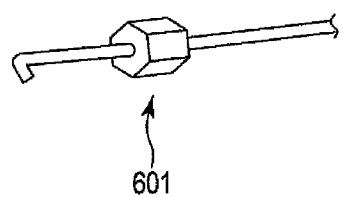
FIG. 20 is a perspective view of the treatment portion (high-frequency knife)

The treatment portion 601 is, for example, an open-shut grip forceps shown in FIG. 18 and FIG. 19, or is a hook knife shown in FIG. 20 or an unshown IT knife. As shown in FIG. 19, the treatment portion 601 and the distal hard portion 11 have indexes 611 that indicate the fitting position of the treatment portion 601 for fitting the treatment portion 601 into the distal opening 31c.

Thus, according to the present embodiment, the common electric bending sheath 2 can be used for various endoscopic treatment tools 600, so that costs can be reduced. Moreover, according to the present embodiment, the wire 603 for coupling the treatment portion 601 to the operation portion 605 is only disposed in the treatment tool insertion channel 31b. Therefore, according to the present embodiment, the treatment tool insertion channel 31b can be smaller in diameter than when the whole endoscopic treatment tool 600 is inserted through the treatment tool insertion channel 31b. As a result, the electric bending sheath 2 can be reduced in diameter.

According to the present embodiment, the treatment portion 601 is fitted in the distal opening 31c. Therefore, if the electric bending sheath 2 is circumferentially rotated, the treatment portion 601 can be rotated, and the operability of the treatment portion 601 can be improved. Moreover, according to the present embodiment, as shown in FIG. 21, it is possible to operate the operation portion 605 while gripping the grip portion 33, so that the operability can be improved.

According to the present embodiment, after use, the treatment portion 601 is removed from the distal opening 31c, the endoscopic treatment tool 600 alone is disposed of, and the electric bending sheath 2 is cleaned. As a result, the electric bending sheath 2 can be reused.

According to the present embodiment, the treatment portion 601 can be easily positioned by the indexes 611 and thus fitted into the distal opening 31c.

When the electric bending sheath 2 comprises an unshown imaging unit, the treatment portion 601 protruding from the distal opening 31c may have indexes which indicate the vertical and horizontal positions and which are imaged by the imaging unit. The indexes are disposed in the vertical and horizontal positions of the treatment portion 601, and indicate the upper side, the lower side, the left side, and the right side. Thus, according to the present embodiment, the bending direction of the electric bending sheath 2 can be easily recognized by checking the indexes imaged by the imaging unit.

Figure 22:
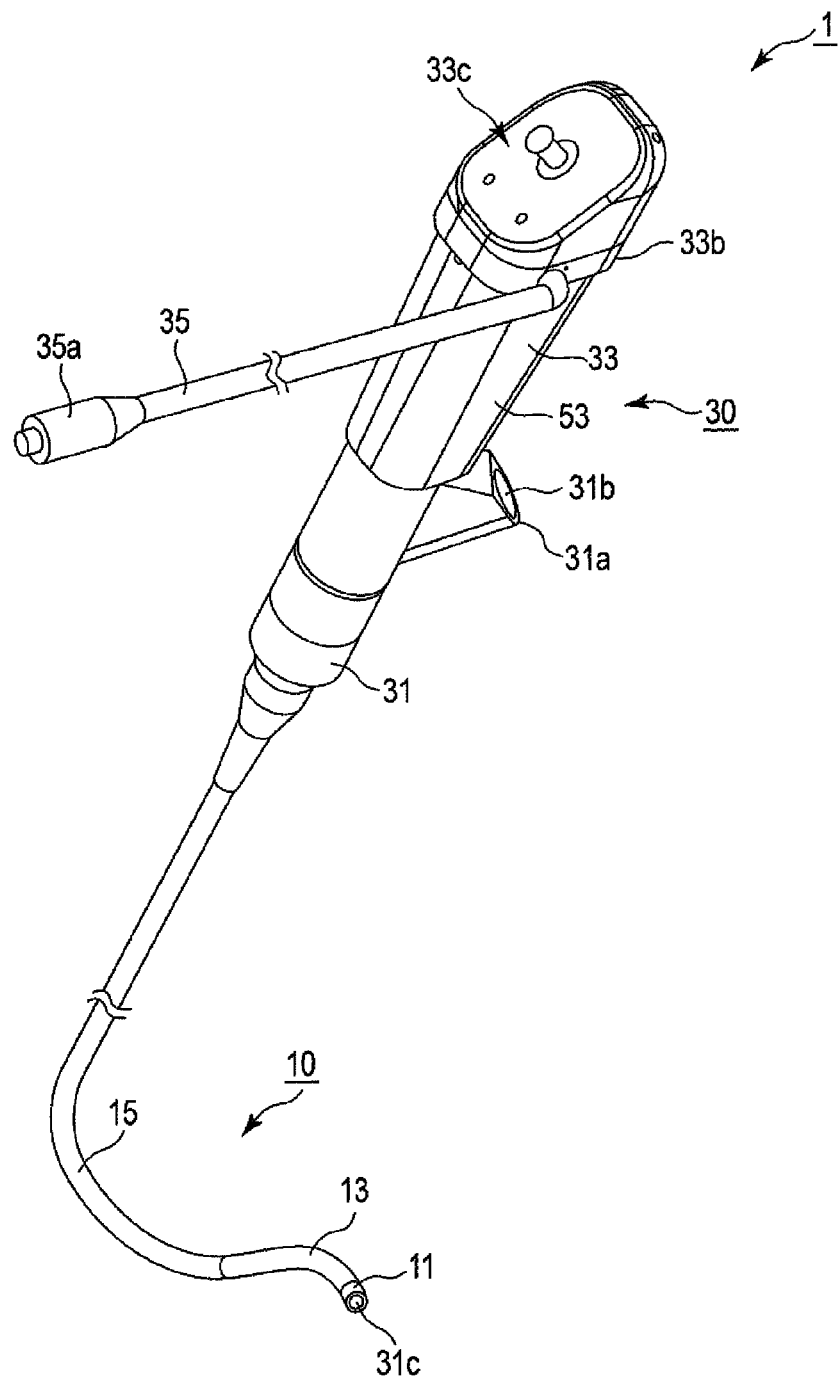
FIG. 22 is a perspective view of the electric bending endoscope in which a bending operation portion is a joystick.

Although the bending operation portion 33c is, for example, the TACT switch in the present embodiment, the bending operation portion 33c is not limited thereto. As shown in FIG. 22, the bending operation portion 33c may be, for example, a joystick.

The present invention is not completely limited to the embodiment described above, and the components can be modified at the stage of carrying out the invention without departing from the spirit thereof. Various inventions can be produced by properly combining the components disclosed in the embodiment described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bending mechanism which vertically and horizontally bends a bending portion disposed in an insertion portion to be inserted into a body cavity, the bending mechanism comprising:
   a base plate comprising a front surface extending along a longitudinal direction of the insertion portion and a rear surface extending along the longitudinal direction of the insertion portion and being opposite to the front surface;
   a vertical driving portion which generates vertical driving force to vertically bend the bending portion and which is disposed in the front surface so that a central axis of the vertical driving portion extends along the longitudinal direction of the insertion portion;
   a horizontal driving portion which generates horizontal driving force to horizontally bend the bending portion and which is disposed in the front surface so that a central axis of the horizontal driving portion extends along the longitudinal direction and is adjacent to the vertical driving portion so as to have a constant distance therebetween;
   a vertical rotary portion which has a central axis arranged on a side of the front surface and coaxial with the central axis of the vertical driving portion, which is coupled to the vertical driving portion and which is rotated around the central axis of the vertical driving portion by the vertical driving force and which is disposed on the side of the front surface;
   a horizontal rotary portion which has a central axis arranged on the side of the front surface and coaxial with the central axis of the horizontal driving portion which is coupled to the horizontal driving portion and which is rotated around the central axis of the horizontal driving portion by the horizontal driving force and which is disposed on the side of the front surface to be adjacent to the vertical rotary portion in the perpendicular direction;

a vertical operation wire, the vertical operation wire being wound around the vertical rotary portion, extending toward the rear surface from the vertical rotary portion and bending to surround an edge portion of the base plate, being disposed along the longitudinal direction in the rear surface, being connected to the bending portion, the vertical operation wire pulling the bending portion and vertically bending the bending portion when the vertical rotary portion is rotated by the vertical driving force;

a horizontal operation wire, the horizontal operation wire being wound around the horizontal rotary portion, extending toward the rear surface and bending from the horizontal rotary portion to surround an edge portion of the base plate, being disposed along the longitudinal direction in the rear surface, being connected to the bending portion, the horizontal operation wire pulling the bending portion and horizontally bending the bending portion when the horizontal rotary portion is rotated by the horizontal driving force; and a holding portion which holds the vertical operation wire extending from the vertical rotary portion and the horizontal operation wire extending from the horizontal rotary portion so that the vertical operation wire extends from the vertical rotary portion to the rear surface on a side where the horizontal rotary portion is disposed and so that the horizontal operation wire extends from the horizontal rotary portion to the rear surface on a side of the vertical rotary portion and further intersects with the vertical operation wire when the vertical operation wire and the horizontal operation wire extend toward the rear surface.

2. The bending mechanism according to claim 1, wherein the vertical driving portion and the horizontal driving portion have the same shape, the vertical rotary portion comprises
a vertical bearing into which a driving shaft of the vertical driving portion is fitted, and
a vertical winding portion which is formed to be integrated with the vertical bearing and which is greater in diameter than the vertical bearing and the vertical driving portion and around which the vertical operation wire is wound, the horizontal rotary portion comprises
a horizontal bearing into which a driving shaft of the horizontal driving portion is fitted, and
a horizontal winding portion which is formed to be integrated with the horizontal bearing and which is greater in diameter than the horizontal bearing and the horizontal driving portion and around which the horizontal operation wire is wound, and one of the vertical winding portion and the horizontal winding portion is disposed closer to the vertical driving portion and the horizontal driving portion than the other so that a part of the vertical winding portion and a part of the horizontal winding portion overlap each other in the insertion direction.

3. The bending mechanism according to claim 2, wherein in the perpendicular direction, the vertical winding portion is adjacent to the horizontal bearing, and the horizontal winding portion is adjacent to the vertical bearing.

4. The bending mechanism according to claim 3, wherein a spiral groove in which the vertical operation wire is disposed is formed in an outer peripheral surface of the vertical winding portion, and a spiral groove in which the horizontal operation wire is disposed is formed in an outer peripheral surface of the horizontal winding portion.

5. The bending mechanism according to claim 4, wherein the holding portion comprises a vertical regulation portion which regulates the extending direction of the vertical operation wire so that the vertical operation wire extends from the vertical winding portion in a tangential direction of the vertical winding portion tilted with respect to the perpendicular direction, a vertical guide portion which prevents interference between the vertical operation wire and the horizontal operation wire when the vertical operation wire regulated by the vertical regulation portion is inserted through the vertical guide portion, the vertical guide portion guiding the vertical operation wire so that the vertical operation wire extends from the vertical winding portion to the rear surface on the side of the horizontal rotary portion, a horizontal regulation portion which regulates the extending direction of the horizontal operation wire so that the horizontal operation wire extends from the horizontal winding portion in a tangential direction of the horizontal winding portion tilted with respect to the perpendicular direction, a horizontal guide portion which prevents interference between the vertical operation wire and the horizontal operation wire when the horizontal operation wire regulated by the horizontal regulation portion is inserted through the horizontal guide portion, the horizontal guide portion guiding the horizontal operation wire so that the horizontal operation wire extends from the horizontal winding portion to the rear surface on the side of the vertical rotary portion and intersects with the vertical operation wire, and a support member which supports the vertical regulation portion and the horizontal regulation portion and which is fixed to the base plate.

6. The bending mechanism according to claim 5, wherein the vertical guide portion and the horizontal guide portion are bendable soft materials.

7. A bending mechanism which is disposed in a base plate and which bends a bending portion disposed in an insertion portion to be inserted into a body cavity, the bending mechanism comprising:

a driving portion which generates driving force to bend the bending portion and which is disposed in a front surface of the base plate so that a central axis of the driving portion extends along the longitudinal direction of the insertion portion;

a rotary portion which has a central axis coaxial with the central axis of the driving portion, which is coupled to the driving portion and which is rotated around the central axis of the driving portion by the driving force and which is disposed on a side of the front surface;

an operation wire, the operation wire being wound around the rotary portion, extending toward a rear surface of the base plate and bending from the rotary portion so as to surround an edge portion of the base plate, being disposed along the longitudinal direction in the rear surface, being connected to the bending portion, the operation wire pulling the bending portion and bending the bending portion when the rotary portion is rotated by the driving force; and a holding portion which holds the operation wire extending from the rotary portion so that one end of the operation wire and the other end thereof intersect with each other when the operation wire extends toward the rear surface.

8. The bending mechanism according to claim 1, wherein the longitudinal direction of the insertion portion is an X-axis direction, a direction perpendicular to the X-axis direction is a Y-axis direction, a direction perpendicular to the X-axis direction and the Y-axis direction is a Z-axis direction, a plane formed by the X-axis direction and the Y-axis direction is an XY plane, a plane formed by the X-axis direction and the Z axis direction is an XZ plane, and a plane formed by the Y-axis direction and the Z-axis direction is an XZ plane;

the vertical operation wire is wound in the X-axis direction by the vertical rotary portion;

the vertical operation wire extends from the vertical rotary portion to the rear surface of the base plate by bending from the YZ plane toward the XY plane;

the horizontal operation wire is wound in the X-axis direction by the horizontal rotary portion; and the horizontal operation wire extends from the horizontal rotary portion to the rear surface of the base plate by bending from the YZ plane toward the XY plane.

9. The bending mechanism according to claim 1, further comprising a grip portion, the grip portion comprising the base plate and a cover portion configured to cover the base plate, wherein the vertical driving portion and the horizontal driving portion are disposed symmetrically about a central axis of the grip portion.

10. The bending mechanism according to claim 1, wherein each of the vertical driving portion and the horizontal driving portion comprises an actuator, and a driving shaft of the vertical driving portion and a driving shaft of the horizontal driving portion are disposed in the longitudinal direction.

11. The bending mechanism according to claim 5, wherein the vertical guide portion and the horizontal regulation portion comprise guide tubes, respectively, and the vertical operation wire and the horizontal operation wire are inserted into the guide tubes, respectively.

* * * * *